United States Patent [19]

Mack

[11] 4,058,543

[45] Nov. 15, 1977

[54] ORGANOTIN MERCAPTO DICARBOXYLIC ACID ESTERS AND COMPOSITIONS

[76] Inventor: Gerry P. Mack, 34-28 86 St., Jackson Heights, N.Y. 11372

[21] Appl. No.: 646,310

[22] Filed: Jan. 2, 1976

[51] Int. Cl.$^2$ ............................ C08K 5/58; C08K 5/36
[52] U.S. Cl. ............................... 260/45.75 S; 252/406; 260/429.7
[58] Field of Search ....................... 260/429.7, 45.75 S

[56] References Cited

U.S. PATENT DOCUMENTS

| | | | |
|---|---|---|---|
| 2,648,650 | 8/1953 | Weinberg et al. | 260/429.7 X |
| 3,640,953 | 2/1972 | Brecker et al. | 260/45.75 S |
| 3,642,677 | 2/1972 | Brecker et al. | 260/45.75 S |
| 3,657,294 | 4/1972 | Glaskey | 260/429.7 |

*Primary Examiner*—Helen M. S. Sneed

[57] ABSTRACT

Organotin mercapto dicarboxylic acid esters are provided having either substantially no odor or a remarkably low odor, and capable of imparting to polyvinyl chloride resin compositions when heated at elevated temperatures an enhanced resistance to early discoloration as well as an enhanced resistance to long term discoloration, without any obnoxious mercaptide odors.

A process is provided for preparing organotin mercapto carboxylic acid esters by reaction of a monohydric alcohol or mixed monohydric alcohol-glycol mercapto dicarboxylic acid ester with an organotin oxide or halide, and then, if the mercapto dicarboxylic acid ester is of a monohydric alcohol only, transesterifying this reaction product with a glycol.

Polyvinyl chloride resin compositions are also provided containing such organotin mercapto carboxylic acid esters, and having an enhanced resistance to both early and long term discoloration, without any obnoxious mercaptide odor.

47 Claims, No Drawings

ORGANOTIN MERCAPTO DICARBOXYLIC ACID ESTERS AND COMPOSITIONS

The stabilizing effectiveness of organotin stabilizers for polyvinyl chloride resins is generally associated with the structure of the organotin groups, a high tin content, and a high sulfur content. For optimum stabilizing effectiveness, all three features become prerequisites and each must be optimum, as well. The manner in which the organotin, tin and sulfur groups are associated in the molecule, however, appears to be more important than high proportions of tin and sulfur.

The organotin sulfides, for example, offer the highest tin and sulfur contents per organotin group, and yet they are not the best stabilizers, and have never found a place as a commercial stabilizer, since they do not impart resistance to development of early discoloration. Despite their considerably lower tin and sulfur contents, the most effective organotin stabilizers presently in widespread use, and the recognized standard for judging other organotin stabilizers, are the organotin mercapto carboxylic acid esters. Despite their stabilizing effectiveness, however, the organotin mercapto carboxylic acid esters have several serious disadvantages.

A further problem associated with the organotin mercapto carboxylic acid esters, especially the dialkyl tin thioglycolate esters, is their tendency to crystallize or precipitate when formulated in liquid polyvinyl chloride resin stabilizer compositions.

The formation of a crystalline precipitate is due to hydrolysis of the organotin thioglycolate ester to form a cyclic compound that is insoluble in the system. The cyclic compound is not an effective stabilizer, and therefore its formation depreciates if not destroys the effectiveness of the organotin mercapto carboxylic acid ester as a stabilizer.

Attempts have been made to overcome this difficulty. Hecker in U.S. Pat. No. 2,789,963, patented Apr. 23, 1957 and Hoch in U.S. Pat. No. 3,655,703, patented Apr. 11, 1972, suggest the addition of various additives. These are helpful, but they merely delay and do not entirely prevent the formation of crystalline precipitates.

A further problem with the organotin mercapto carboxylic acid esters is their odor, which to some tastes can only be described as appalling. This ordor is so obnoxious that during processing, even under ventilation, the order cannot be removed, and remains with the finished resin articles for a long time.

H. Verity Smith in his pamphlet entitled *The Development of the Organotin Stabilizers*, page 19, refers to this ordor, but the fact is that because of their stabilizing effectiveness the organotin mercapto carboxylic acid esters have been doggedly endured. This is partly because the other organotin stabilizers that are available either have a worse odor, or are considerably less effective, so that their use in sufficiently large amounts posed other and more difficult problems.

A further problem with the organotin mercapto carboxylic acid esters is their inability to entirely prevent an early yellow discoloration in the resin, which is manifested before severe heat deterioration really sets in. Weisfeld U.S. Pat. No. 3,640,650, patented Feb. 8, 1972 proposed the use of mono alkyl tris (alkyl thioglycolates) in an attempt to improve early color. This early discoloration has not been considered disadvantageous for many uses, and the efforts of most workers in this field have been directed towards minimizing the onset of the more serious heat deterioration which sets in during long heating, as in milling. However, because of this discoloration, and the accompanying haziness that may also appear, it has not been possible in all cases to obtain a substantially clear and colorless polyvinyl chloride resin composition using these stabilizers.

There has been a need for a PVC stabilizer that will provide a compound having no initial discoloration or yellowing, and maintaining this freedom from early yellowing through its manufacturing cycle of five to fifteen minutes, as for instance, in PVC containers such as bottles. This is because the average period of time during which a given amount of resin product remains in the processing equipment, even in a continuous process which includes recycling of portions of the worked product, is less than fifteen minutes. Only a minor proportion of the resin will be subjected to working temperatures for periods of up to one-half hour or longer. Hence, the preservation of a good color and clarity during the first fifteen minutes of heating can be more difficult than the protection of the relatively small proportion of the resin by long term heat stabilizers, such as the organotin mercapto carboxylic acid esters.

The use of the organotin mercapto carboxylic acid esters as stabilizers for polyvinyl chloride resins is well known, and is set forth in such early patents as U.S. Pat. No. 2,752,325 to Leistner et al., patented June 26, 1956, 2,641,596 to Leistner et al, patented June 9, 1953, and 2,648,650 to Weinberg et al, patented Aug. 11, 1953.

Similar disclosures of polymeric organotin compounds, which generally include a chain of tin atoms connected through oxygen or sulfur atoms, are set out in U.S. Pat. Nos. 2,597,920, patented Apr. 15, 1962; 2,626,953, patented Jan 27, 1953; 2,628,211, patented Feb. 10, 1953; 3,184,430 patented May 18, 1965; and 2,938,013, patented May 24, 1960.

U.S. Pat. No. 2,809,956, patented Oct. 15, 1957, discloses polymeric organotin compounds which include mercapto ester groups attached to tin, having the general formula:

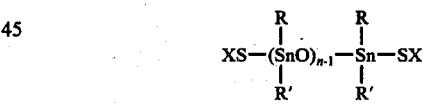

wherein SX can be mercapto; mercapto alcohol or ester; or mercapto acid ester groups. These compounds, however, have been found not to be as effective stabilizers as the monomeric organotin mercapto carboxylic acid esters, such as dibutyltin bis-(isooctyl thioglycolate).

Weinberg and Johnson U.S. patent No. 2,832,752, patented April 29, 1958, describe organotin compounds which are condensation products with polycarboxylic mercapto acids and esters containing the group

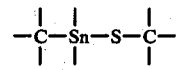

The class of compounds in question is indicated by the formula

where R is aryl, alkyl or alkaryl, such as methyl, ethyl, butyl, propyl, phenyl, tolyl, benzyl, etc.; R' is aliphatic hydrocarbon radical, R" is hydrogen, aryl, alkyl, alkaryl or cyclic, saturated or unsaturated, m is an integer not less than 2, and n may be 1, 2, or 3. Among the groups from which R" may be selected are isooctyl, 2-butyloctyl, butyl, cyclohexyl, dihydroabietyl, benzyl, phenyl, cresyl, allyl. Among the polycarboxylic acids and their esters which may be employed in this invention are thiomalic acid, α-mercaptoadipic acid, and their appropriate esters.

Example II provides dibutyltin-S,S'-bis-(thiomalic acid) and Example I, dibutyltin-S,S'-bis(dibutyl thiomalate), the former a low-melting solid, and the latter a viscous amber liquid, both of which were however quite deficient in tin and sulfur as compared to the theoretical tin and sulfur contents of the compounds hypothecated. Clearly, the compounds did not correspond to this structure because the tin and sulfur contents were far too low. Dibutyltin-S,S'-bis(thiomalic acid) even when prepared to substantially the correct analysis does not give the freedom from early yellow discoloration and the longterm heat stabilization of the compounds of this invention. The theoretical values for dibutyltin-S,S'-bis-(dibutyl thiomalate) are 15.8% Sn and 8.5%S, or roughly double the quantities found by Weinberg et al for this product.

This type of organotin thiomalate ester has a foul ordor, similar to the organotin mercapto carboxylic esters, and definitely no improvement. These compounds likewise do not overcome the deficiency in the organotin mercapto carboxylic esters of not providing an enhanced resistance to early discoloration.

Mack and Parker U.S. Pat. No. 2,914,506, patented Nov. 24, 1959, provides organotin mercaptides of the formula

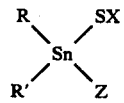

wherein R, R', SX and Z have the following significance: R and R' may be different monovalent hydrocarbon radicals, but will be generally the same radicals, because the starting materials for the preparation of the organo-tin mercapto compounds will be generally the di-(or tri-) hydrocarbon tin halides or oxides available in commerce. The nature of these groups has in most cases no, or only a very minor, influence on the properties of the end products. R and R' may be aliphatic, aromatic, or alicyclic groups, such as methyl, ethyl, propyl, butyl, amyl, hexyl, octyl, lauryl, allyl, benzyl, phenyl, tolyl, cyclohexyl.

SX may be, for instance, the rest of a mercaptan, of a mercapto alcohol, or of an ester of a mercapto alcohol or mercapto acid.

Readily available mercapto acid esters are the esters of thioglycolic acid, such as ethyl thioglycolate, and generally the esters of mono and dibasic aliphatic and aromatic mercapto acids, such as esters of beta thiopropionic acid, thiolactic acid, thiobutyric acid, alpha mercapto lauric acid, thiomalic acid, thiosalicylic acid, and the like.

Z may have the same composition as SX. Thus, the broad class of compounds defined by this formula encompass the organotin thiomalate esters of the type disclosed by Weinberg et al in U.S. Pat. No. 2,832,752, but in fact no organotin thiomalate esters are named or disclosed in any working Example. A compound R₂SN(SX)Z where R is n-butyl, SX is derived from dibutyl thiomalate and Z is derived from isooctyl thioglycolate, an instance of the compounds shown in U.S. Pat. No. 2,914,506, was lacking in the ability to prevent early yellow discoloration and also formed a precipitate within 50 days storage at room temperature.

Brecker U.S. Pat. No. 3,565,931, and Kauder No. 3,565,930, both patented Feb. 23, 1971, describe organotin mercapto carboxylic acid ester sulfides having a high concentration of tin, in the range from about 18 to about 35% by weight, and a high concentration of sulfur, within the range from about 10 to about 25% sulfur. These compounds have a relatively high concentration of tin and sulfur, compared to the organotin mercapto carboxylic acid esters, and are said to improve the initial color of a resin composition during the first 30 minutes of heating, and to also improve the long term stability before final charring. However, the odor of these compositions offers no advantage over the organotin mercapto carboxylic acid esters.

Cohen U.S. Pat. No. 3,627,716, patented Dec. 14, 1971, and Brecker No. Pat. No. 3,642,677, patented Feb. 15, 1972 describe stabilizer compositions for polyvinyl chloride resins comprising an organotin mercapto carboxylic acid ester, a bivalent stannous tin salt, and, optionally, a diorganotin oxide. The stannous salts are acid to impart to the organotin mercapto carboxylic acid esters the ability to improve the resistance of polyvinyl chloride resins to the development of early discoloration when heated at elevated temperatures.

In accordance with the present invention, organotin mercapto dicarboxylic acid esters and especially organotin thiomalate esters are provided having either substantially no odor or a remarkably low odor, that prevent the development of early discoloration of polyvinyl chloride resins when heated at elevated temperatures. The organotin thiomalate esters of the invention are superior in these respects to the organotin mercapto carboxylic acid esters. In addition, these organotin thiomalate esters show no tendency to crystallize or develop precipitates in liquid stabilizer compositions for polyvinyl chloride resins.

In total stabilizing effectiveness they are superior to the organotin mercapto carboxylic acid esters. Thus, these organotin thiomalate esters are unsually advantageous stabilizers for polyvinyl chloride resin compositions. Other organotin mercapto dicarboxylic acid esters are advantageous in these respects as well, such as organotin mercapto methyl succinic acid esters.

The organotin mercapto dicarboxylic acid esters of the invention are mixed monohydric and polyhydric alcohol esters of organotin mercapto dicarboxylic acid salts having per tin atom one or two alkyl, cycloalkyl, or alkylcycloalkyl groups attached to tin through carbon, and having from one to about twelve carbon atoms; and two or three mercapto dicarboxylic acid ester groups attached to tin through sulfur, the mercaptodicarboxylic acid having from about 4 to about 24 carbon atoms, and having at least one esterifying group selected from the group consisting of alkyl, cycloalkyl, and alkylcycloalkyl having from one to about 12 carbon atoms, and at least one esterifying group selected from the group consisting of bivalent alkylene, cycloalkylene and alkylenecycloalkylene having from about 2 to about 12 carbon atoms, such bivalent groups linked to hydroxyl, and such bivalent groups linked to a second organotin mercapto dicarboxylic acid ester group. These compounds have been assigned the following general formula:

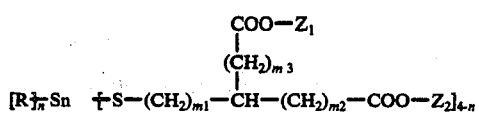

wherein
- $m_1$ and $m_3$ are numers within the range from 0 to about 7;
- $m_2$ is a number within the range from 1 to about 7;
- $n$ is 1 or 2;
- R is selected from the group consisting of alkyl, cycloalkyl, and alkylcycloalkyl having from one to about twelve carbon atoms linked to tin through carbon; and
- at least one of $Z_1$ and $Z_2$ is selected from the group consisting of alkyl, cycloalkyl and alkylcycloalkyl having from three to about 12 carbon atoms;
- and at least one of $Z_1$ and $Z_2$ is selected from the group consisting of
  i. bivalent alkylene, cycloalkylene and alkylenecycloalkylene having from two to about twelve carbon atoms;
  ii. hydroxyalkyl, hydroxycycloalkyl and hydroxyalkylcycloalkyl having from two to about twelve carbon atoms; and
  iii. bivalent alkylene, cycloalkylene and alkylenecycloalkylene having from about two to about twelve carbon atoms and linked to a second organotin mercapto dicarboxylic acid ester group of Formula 1 via an ester group thereof of the form:

$$-Y-OOC(CH_2)_{m2}-\underset{\underset{COOZ_1}{|}}{\underset{(CH_2)_{m3}}{|}}CH(CH_2)_{m1}-S-$$

iv. bivalent alkylene, cycloalkylene, and alkylenecycloalkylene linked to a second organotin thiomalate group of Formula I via an ester group thereof of the form:

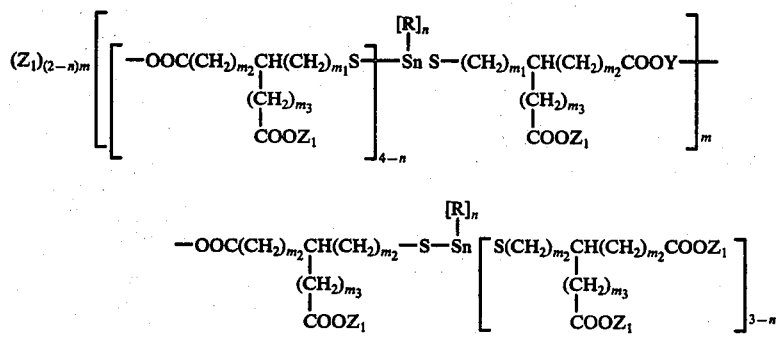

It will be apparent that when $m_1$ and $m_3$ are 0 and $m_2$ is 1, the ester is a thiomalate ester. The thiomalate esters are preferred. When $m_1$ and $m_2$ are 1 and $m_3$ is 0, the ester is a mercaptomethylsuccinate ester. When $m_1$, $m_2$, and $m_3$ are each 1, the ester is a β-mercaptomethyl glutarate ester, and when $m_1$ is 0, and $m_2$ and $m_3$ are each 1, the ester is a β-mercaptoglutarate ester. Similarly, α-mercaptoglutarate, α- and β-mercaptoadipate, α-, β- and γ- and δ-mercaptoazelate and mercaptosebacate esters are obtained.

When $m_1$ and $m_3$ are 0, $m_2$ is 1, and when
(1) $n$ is 1, the compounds take the form

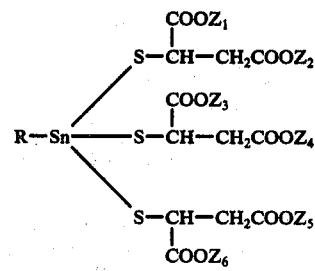

and when
(2) $n$ is 2, the compounds take the form:

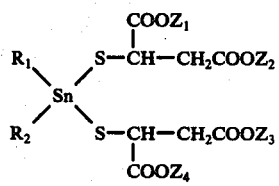

In these formulae, $Z_1$, $Z_2$, $Z_3$, $Z_4$, $Z_5$ and $Z_6$ are the same as $Z_1$ and $Z_2$ as defined above.

It will be apparent from the above that when $Z_1$, $Z_2$, $Z_3$, $Z_4$, $Z_5$ and $Z_6$ are all either monoalkyl, monocycloalkyl, or monoalkylcycloalkyl of (i), or hydroxyalkyl, hydroxycycloalkyl or hydroxyalkylcycloalkyl, $m_1$ and $m_3$ are 0 and $m_2$ is 1, the formula takes one of the two forms, according to whether $n$ is 1 or $n$ is 2:

n = 1:

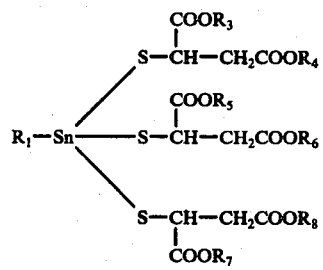

n = 2:

-continued $$R_1 \diagdown_{Sn} \diagup^{S-CH-CH_2COOR_4}_{|\,COOR_3} \\ R_2 \diagup \diagdown_{S-CH-CH_2COOR_5}_{|\,COOR_6}$$

wherein:

$R_1$ and $R_2$ are selected from the group consisting of alkyl, cycloalkyl or alkylcycloalkyl having from one to about 12 carbon atoms; and $R_3$, $R_4$, $R_5$, $R_6$, $R_7$ and $R_8$ (and $R_{10}$ and $R_{11}$ below) are selected from the group consisting of alkyl, cycloalkyl and alkylcycloalkyl having from 1 to about 12 carbon atoms; and hydroxyalkyl, hydroxycycloalkyl, and hydroxyalkylcycloalkyl having from 2 to about 12 carbon atoms.

When one of $Z_1$ and $Z_2$; $Z_3$ and $Z_4$; and $Z_5$ and $Z_6$ is monovalent alkyl, cycloalkyl or alkylcycloalkyl, and the other two Z's are taken together as a bivalent alkylene cycloalkylene or alkylcycloalkylene, $m_1$ and $m_3$ are 0, and $m_2$ is 1, the formula takes one of the two forms according to whether $n$ is 1 or $n$ is 2:

n = 1:

IIIa)(i)

$$R_1-Sn \diagdown \begin{matrix} S-CH-CH_2COO \\ |\,COOR_3 \\ \\ S-CH-CH_2COO \\ |\,COOR_6 \\ |\\ COOR_{10} \\ S-CH-CH_2COOR_{11} \end{matrix} \diagup R_9$$

n = 1:

IIIb)(i)

$$R_1-Sn \diagdown \begin{matrix} S-CH-COO \\ |\,CH_2COOR_3 \\ \\ S-CH-COO \\ |\,CH_2COOR_6 \\ \\ S-CH-COOR_{10} \\ |\,CH_2COOR_{11} \end{matrix} \diagup R_9$$

n = 2:

IIIa)(ii)

$$\begin{matrix} R_1 \\ \diagdown \\ R_2 \diagup \end{matrix} Sn \diagdown \begin{matrix} S-CH-CH_2COO \\ |\,COOR_3 \\ \\ S-CH-CH_2COO \\ |\,COOR_6 \end{matrix} \diagup R_9$$

n = 2:

IIIb)(ii)

$$\begin{matrix} R_1 \\ \diagdown \\ R_2 \diagup \end{matrix} Sn \diagdown \begin{matrix} S-CH-COO \\ |\,CH_2COOR_3 \\ \\ S-CH-COO \\ |\,CH_2COOR_6 \end{matrix} \diagup R_9$$

wherein $R_1$, $R_2$, $R_3$, $R_6$, $R_{10}$ and $R_{11}$ are as above, and $R_9$ is a bivalent alkylene, cycloalkylene or alkylenecycloalkylene group having from 2 to about 12 carbon atoms.

When one of $Z_1$, $Z_2$, $Z_3$, $Z_4$, $Z_5$ and $Z_6$ is an alkylene, cycloalkylene or alkylenecycloalkylene group linked to a second organotin thiomalate group, $m_1$ and $m_3$ are 0, and $m_2$ is 1, the formula takes one of the two forms, according to whethe $n$ is 1 or $n$ is 2:  IIb)

n = 1:

IVa)(i)

$$R_1-Sn \diagdown \begin{matrix} S-CH\!-\!-\!CH_2COOR_9OOC\!-\!-\!CH_2CHS \\ |\,COOR_3 \qquad\qquad\qquad\qquad COOR_3 \\ \\ [S-CH-CH_2COOR_5]_2[R_5OOC-CH_2CHS]_2 \\ |\,COOR_6 \qquad\qquad\qquad\qquad COOR_6 \end{matrix} \diagup Sn-R_1$$

n = 1:

IVb)(i)

$$R_1-Sn \diagdown \begin{matrix} CH_2COOR_3 \qquad\qquad CH_2COOR_3 \\ S-CH\!-\!-\!COOR_9OOC\!-\!-\!CH-S \\ \\ [S-CH-COOR_5]_2 \; [R_5OOC-CHS]_2 \\ |\,CH_2COOR_6 \qquad\qquad CH_2COOR_6 \end{matrix} \diagup Sn-R_1$$

n = 2:

IVa)(ii)

$$\begin{matrix} R_1 \\ \diagdown \\ R_2 \diagup \end{matrix} Sn \diagdown \begin{matrix} S-CHCH_2COOR_9OOCCH_2CHS \\ |\,COOR_3 \qquad\qquad\qquad COOR_3 \\ \\ S-CHCH_2COOR_5R_5OOCCH_2CHS \\ |\,COOR_6 \qquad\qquad\qquad COOR_6 \end{matrix} \diagup \begin{matrix} R_1 \\ Sn \\ R_2 \end{matrix}$$

n = 2:

IVb)(ii)

$$\begin{matrix} R_1 \\ \diagdown \\ R_2 \diagup \end{matrix} Sn \diagdown \begin{matrix} CH_2COOR_3 \qquad CH_2COOR_3 \\ S-CHCOOR_9OOCCHS \\ \\ S-CHCOOR_5R_5OOCCHS \\ CH_2COOR_6 \qquad CH_2COOR_6 \end{matrix} \diagup \begin{matrix} R_1 \\ Sn \\ R_2 \end{matrix}$$

IIa)

wherein:

$R_1$, $R_2$, $R_3$, $R_5$ and $R_6$ are as above and $R_9$ is a bivalent alkylene, cycloalkylene or alkylenecycloalkylene group having from 2 to about 12 carbon atoms.

When two of $Z_1$, $Z_2$, $Z_3$, $Z_4$, $Z_5$ and $Z_6$ are bivalent alkylene, cycloalkylene or alkylenecycloalkylene groups linked to a second organotin thiomalate group, $m_1$ and $m_3$ are 0, and $m_2$ is 1, the formula takes one of the two forms, according to whether $n$ is 1 or $n$ is 2:

n = 1:

Va)(i)

$$R_1-Sn \diagdown \begin{matrix} COOR_3 \qquad\qquad\qquad COOR_3 \\ [S-CH\!-\!-\!CH_2COOR_9OOC\!-\!-\!CH_2CHS]_2 \\ \\ S-CH-CH_2COOR_5R_5OOC-CH_2-CH-S \\ |\,COOR_6 \qquad\qquad\qquad\qquad COOR_6 \end{matrix} \diagup Sn-R_1$$

n = 1:

Vb)(i)

$$R_1-Sn \diagdown \begin{matrix} CH_2COOR_3 \qquad CH_2COOR_3 \\ [S-CH-COOR_9\,OOC-CH-S]_2 \\ \\ S-CH-COOR_5\,R_5OOC-CH-S \\ |\,CH_2COOR_5 \qquad\qquad CH_2COOR_6 \end{matrix} \diagup Sn-R_1$$

-continued n = 2:

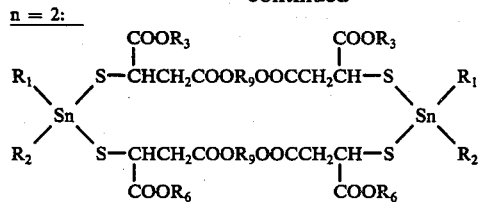 Va)(ii)

n = 2:

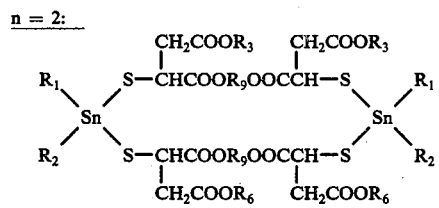 Vb)(ii)

wherein:

$R_1$, $R_2$, $R_5$, $R_6$ and $R_9$ are as above.

It is also possible to obtain polymers in the case where the glycol reacts with carboxylic acid or ester groups of different organotin thiomalate ester molecules, of the types:

n = 1:

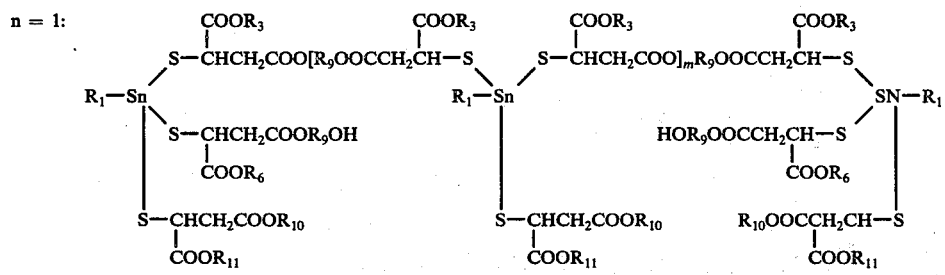 VI a)(i)

n = 1:

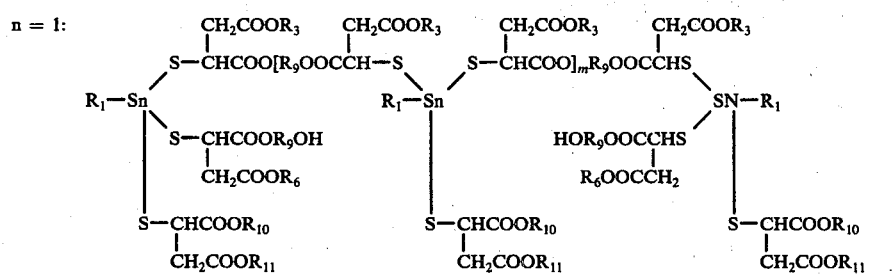 VI b)(i)

n = 2:

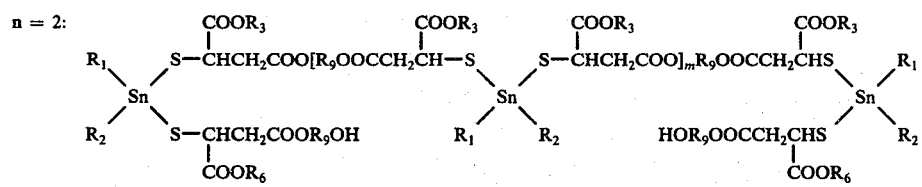 VI a)(ii)

n = 2:

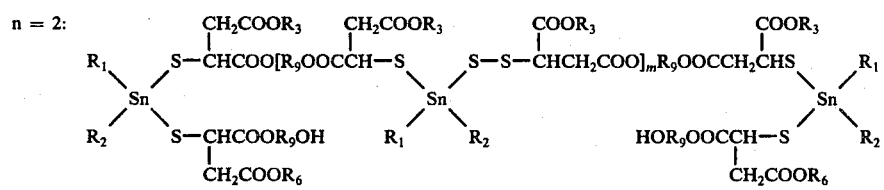 VI b)(ii)

In these polymers, m is a number, which can represent an average number, within the range from about 1 to about 20, but usually not exceeding about 10, and $R_1$, $R_2$, $R_6$, $R_9$, $R_{10}$ and $R_{11}$ are as above.

Other variations within the general Formula I will be apparent to those skilled in this art, but the above variations II to VI exemplify preferred embodiments of the organotin thiomalate esters of the invention. Similar embodiments exist of the other organotin mercapto dicarboxylic acid esters.

Exemplary $Z_1$, $Z_2$, $Z_3$, $Z_4$, $Z_5$, $Z_6$, $R_1$, $R_2$, $R_3$, $R_4$, $R_5$, $R_6$, $R_7$, $R_8$, $R_{10}$, and $R_{11}$ alkyl groups include methyl, ethyl, n-propyl, isopropyl, n-butyl, secondary butyl, tertiary butyl, isobutyl, isoamyl, secondary amyl, and tertiary amyl, n-hexyl, isohexyl, n-heptyl, n-octyl, isooctyl, 2-ethyl hexyl, n-nonyl, n-decyl, n-undecyl and n-dodecyl. The octyl isomers are preferred for Rn-Sn- when the organotin thiomalate esters of the invention are to be utilized in foodstuff applications, because of their low toxicity.

Exemplary cycloalkyl cycloalkyl groups include cyclopentyl, cyclohexyl, cyclobutyl, cyclopropyl, cycloheptyl, cyclooctyl, and cyclododecyl. Alkylcycloalky groups include ethyl cyclohexyl, diethylcyclohexyl, tetra methyl cyclohexyl, propyl, cyclopentyl, methyl cyclopentyl, tetra methyl cyclopentyl, trimethyl cyclobutyl, and diethyl cycoheptyl.

The $Z_1$, $Z_2$, $Z_3$, $Z_4$, $Z_5$, $Z_6$, $R_3$, $R_4$, $R_5$, $R_6$, $R_7$, $R_8$, $R_{10}$, and $R_{11}$ hydroxyalkyl groups are derived from alkylene glycols having from two to about twelve carbon atoms, for example, ethylene glycol; 1,2- and 1,3- propylene glycol; 1,2-; 2,3-; 1,3-; and 1,4- butylene glycol; 1,2-; 2,3-; 2,4-; 1,5-; and 1,4- amylene glycol, 1,6- hexylene glycol, 2,4-dimethyl pentanediol, dodecylene glycol, decylene glycol, and octylene glycol; and cycloalkylene and alkylenecycloalkylene glycols having from three to about twelve carbon atoms, for example, cyclobutylene glycol, cyclopentylene glycol, cyclohexylene glycol, cycloheptylene glycol, cyclooctylene glycol, 1,4-cyclohexane dimethanol, 1,4-bis-(methylene) cyclohexylene glycol, 1,3-bis-(ethylene) cyclopentylene glycol, and 1,4-bis-(methylene heptylene glycol, in which only one of the two hydroxyl groups is esterified with a thiomalic acid ester group.

If both hydroxyl groups of the glycol are esterified with thiomalic acid ester groups, the compounds are dimers or higher polymers having two or more organotin units, and are of the type of Formulas IV, V and VI above, or have heterocyclic rings of the type of Formula III, above.

The organotin mercapto dicarboxylic acid esters of the invention are readily prepared by two routes. In one route, the corresponding organotin halide is reacted with a monohydric alcohol mercapto dicarboxylic acid ester, followed by transesterification with the desired glycol. The reaction proceeds in accordance with the following scheme:

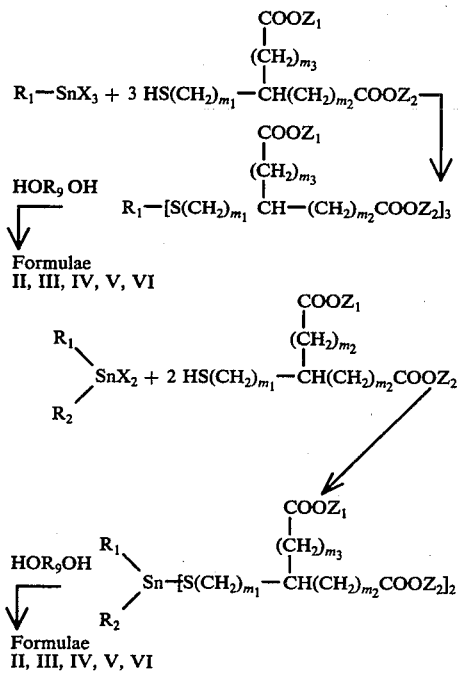

In the second route, the mixed monohydric alcohol glycol mercapto dicarboxylic acid ester is reacted with organotin oxide, or organotin halide with acid acceptor. The compounds of Formulae II, II, IV, V, and VI are then obtained in one step.

When an organotin halide is used with an acid acceptor, the halide can be chloride, bromide or iodide, and the acid acceptor can be any of ammonium, sodium, potassium, lithium, calcium, and magnesium hydroxides, carbonates, and bicarbonates, in aqueous or non-aqueous media. In a non-aqueous reaction medium (no solvent at all or any convenient organic solvent), the halide salt side product can be removed by filtration or subsequent water washing.

Organotin intermediates other than halides or oxides also can be used, including the adducts of ammonia and organic amines with dialkyltin dichlorides, for example $Bu_2SnCl_2 \cdot 2NH_3$, used preferably in an organic solvent medium from which the ammonium chloride side product is filtered off, also dialkyltin dialcoholates such as dibutyltin dimethoxide (from which alcohol side product can be distilled or washed out) or organotin salts of low molecular weight carboxylic acids, e.g. dibutyltin diacetate and tetrabutyl diacetoxy distannoxane, from which acetic acid side product can be distilled or washed out.

It will be apparent that the direction of the reaction towards formation of any particular compound or mixture of Formulae II, III, IV, V, VI is determined by the relative molar proportions of the reactants, according to conventional principles of stoichiometry.

While stoichiometric proportions can be used, according to the product desired, it may be advantageous to depart to some extent from such proportions. Where an excess of mercapto dicarboxylic acid ester is used, the resulting product is a mixture of the organotin compounds stoichiometrically expected with the excess mercapto dicarboxylic acid ester. Excess organotin compound reagents on the other hand can give a variety of products.

When the organotin compound reagent is an organotin oxide, a greater than equivalent amount of oxide can react with an equivalent of mercapto dicarboxylic acid ester to form an overbased product that can be formulated either as an adduct:

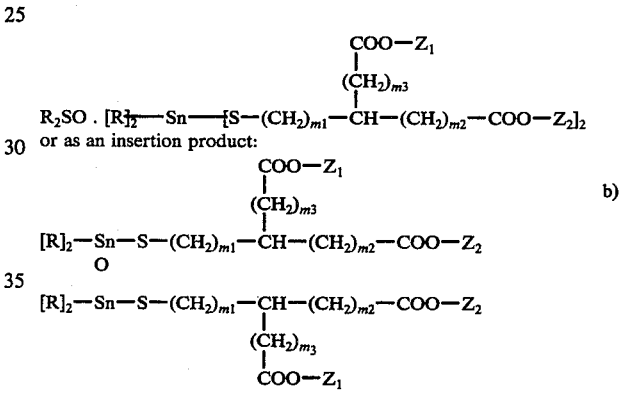

and similarly for RSn compounds.

A reaction product of dibutyltin oxide with thiomalate ester containing S:Sn ratio of 1:1 mixed with one more equivalent of mercapto dicarboxylic acid ester give the product of Formula I. By the same technique, many different S:Sn ratio products between 1:1 and 2:1 can be prepared, and good heat stabilizing activity is obtainable at least in the range of 1.3:1 S:Sn and up.

When the organotin compound reagent is an organotin chloride, and a greater than equivalent amount is used with the mercapto dicarboxylic acid ester, different kinds of product can be obtained, depending on the amount of alkali used. If the amount of alkali is exactly equivalent to the amount of mercapto dicarboxylic acid ester, the excess chloride will remain as $Cl-SnR_2-S-$ or

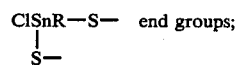 end groups;

if the amount of alkali is equivalent to the amount of chloride, i.e. 3 moles per $RSnCl_3$ and 2 moles per $R_2SnCl_2$, then the products will be the overbased materials obtained with organotin oxide in excess; finally, if the amount of alkali is more than equivalent to the amount of mercapto dicarboxylic acid ester and less than equivalent to the amount of organotin chloride, some of each kind of product will be formed.

The reaction of the thiomalic acid ester with the organotin oxide or halide is conventional, and proceeds in the presence or absence of a solvent, at a moderate temperature, within the range from about 25 to about 150° C, in a relatively short time, of the order of from 20 minutes to 3 hours. According to the value of $n$ in Formula I, two or three moles of the mercapto dicarboxylic acid are used per mole of organotin oxide halide. Any halide can be used, but the chloride, bromide and iodine are more readily available, and would generally be employed.

The transesterification reaction proceeds at an elevated temperature within the range from about 75° to about 200° C, in the absence of a catalyst, with removal of the monohydric alcohol that is displaced by the glycol in the course of the transesterification. Removal of the monohydric alcohol by distillation, preferably by vacuum stripping, ensures that the transesterification reaction proceeds to completion. As the reaction proceeds, the reaction mixture usually increases in viscosity.

The rate of transesterification may be increased in the presence of transesterification catalyst, such as an acid or a base, for example, p-toluene sulfonic acid.

The following Examples represent preferred embodiments of the organotin mercapto carboxylic acid esters in accordance with the invention and their preparation.

EXAMPLE I

Two moles (524 g) dibutyl thiomalate and one mole dimethyltin dichloride (220 g) were mixed and two moles aqueous 10% sodium hydroxide solution then added slowly. The reaction temperature was held at 60° C for one half hour after the addition of the sodium hydroxide solution was complete. The final pH of the reaction mixture was 5.7.

The mixture was separated easily at 60° C in a separatory funnel. The organic portion, the lower layer, was dried and vacuum stripped at 20 to 25 mm of mercury to a maximum pot temperature of 60° C. When all of the water had been removed, the product was filtered, giving a clear, light product, identified as dimethyltin bis-(dibutyl thiomalate).

The dimethyltin bis-(dibutyl thiomalate) was then mixed with ethylene glycol as noted in Table I below in the proportion of one mole ethylene glycol per mole of dimethyltin bis-(dibutyl thiomalate), and the mixture then heated for three hours at from 120° to 125° C. At the conclusion of this reaction time, the butanol liberated in the course of transesterification with ethylene glycol was removed by vacuum-stripping to 130° C maximum pot temperature.

As the reaction proceeded, and the initially immiscible ethylene glycol was transesterified, the reaction mixture became clear, and after the removal of butanol remained clear. In the course of vacuum-stripping, unreacted ethylene glycol was also distilled off, and consequently the transesterification product was considered to be free of both unreacted ethylene glycol and butanol.

Four runs were made under these conditions, with the following results:

TABLE I

| Run No. | Butanol Distilled Moles Per Mole Of Dimethyltin Bis-(Dibutyl Thiomalate) | Butanol Distilled Moles Per Mole Of Ethylene Glycol Reactant |
|---|---|---|
| Run 1 | 1.22 | 1.22 |
| Run 2 | 1.52 | 1.52 |
| Run 3 | 0.70 | 1.09 |
| Run 4 | 1.45 | 1.45 |

EXAMPLES II TO VIII

Two moles (524 g) dibutyl thiomalate and one mole dibutyltin oxide (249 g)(in Example III, a 1:1 mixture of dibutyltin oxide and monobutyltin oxide was used instead) were mixed, and the reaction mixture held at 60° C for one half hour after the addition of the oxide was complete. The reaction mixture was dried and vacuum-stripped at 20 to 25 mm of mercury to a maximum pot temperature of 90° C. When all the reaction water had been removed, the product was filtered, giving a clear, light product, identified as dibutyl bis-(dibutyl thiomalate) (or, in Example III, a 1:1 mixture of this with monobutyltin tris-(dibutyl thiomalate)).

The dibutyltin bis-(dibutyl thiomalate) or, in Example III, a 1:1 mixture of this with monobutyltin tris-(dibutyl thiomalate) was then mixed with the alkylene glycol noted in Table II below in the proportion noted of alkylene glycol per mole of dibutyltin bis-(dibutyl thiomalate) (or, in Example III, a 1:1 mixture of this with monobutyltin tris-(dibutyl thiomalate)) and the mixture then heated for three hours at from 120° to 125° C. At the conclusion of this reaction time, the butanol liberated in the course of transesterification with the alkylene glycol was removed by vacuum-stripping to 130° C maximum pot temperature.

As the reaction proceeded, and the initially immiscible alkylene glycol was reacted, the reaction mixture became clear, and after the removal of butanol remained clear. In the course of vacuum-stripping, unreacted alkylene glycol was also distilled off, and consequently, the transesterification product was considered to be free of both unreacted alkylene glycol and butanol.

Seven organotin thiomalate esters were made under these conditions with the alkylene glycols noted in Table II, with the following results:

TABLE II

| Example No. | Alkylene Glycol Charged Moles/Mole Organotin | Butanol Distilled Moles/Mole Of: | | % Sn |
|---|---|---|---|---|
| | | Mono Or Dibutyltin Bis Or Tris (Dibutyl Thiomalate) | Alkylene Glycol Reactant | |
| II | Ethylene Glycol 0.5 | 0.74 | 1.48 | 16.0 |
| III | Ethylene Glycol 0.5 | 0.86 | 1.71 | 15.8 |
| IV | Ethylene Glycol 1.0 | 1.65 | 1.65 | 16.7 |
| V | Ethylene Glycol 4.0 | 1.98 | 1.225 | 16.3 |
| VI | 1,3-Butylene Glycol 0.5 | 0.71 | 1.42 | 15.7 |
| VII | 1,4-Butylene Glycol 1.0 | 1.83 | 1.83 | 16.4 |
| VIII | Neopentylene Glycol 1.0 | 1.45 | 1.45 | 15.5 |

EXAMPLES IX to XIII

Two moles (524 g) dibutyl thiomalate and one mole dioctyltin dichloride (416 g) were mixed, and two moles aqueous 10% sodium hydroxide solution then added slowly. The reaction temperature was held at 60° C for one half hour after the addition of the sodium hydroxide solution was complete. The final pH of the reaction mixture was 5.7.

The mixture was separated easily at 60° C in a separatory funnel. The organic portion, the lower layer, was dried and vacuum-stripped at 20 to 25 mm of mercury to a maximum pot temperature of 60° C. When all of the water had been removed, the product was filtered, giving a clear, light product, identified as dioctyltin bis-(dibutyl thimalate).

The dioctyltin bis-(dibutyl thiomalate) was then mixed with the alkylene glycol noted in Table III in the proportion noted of alkylene glycol per mole of dioctyltin bis-(dibutyl thiomalate) and the mixture then heated for three hours at from 120° to 125° C. At the conclusion of this reaction time, the butanol liberated in the course of transesterification with alkylene glycol was removed by vacuum-stripping to 130° C maximum pot temperature.

As the reaction proceeded the initially immiscible alkylene glycol dissolved in the reaction mixture, and the product, after the removal of butanol, remained clear. In the course of vacuum-stripping, unreacted alkylene glycol was also distilled off, and consequently the transesterification product was considered to be free of both unreacted glycol and butanol.

Five runs were made under these conditions with the following results:

TABLE III

| Example No. | Glycol Charged Moles/Mole Organotin | Butanol Distilled Moles/Mole Of: | | |
|---|---|---|---|---|
| | | Dioctyltin Bis-(Dibutyl Thiomalate) | Alkylene Glycol Reactant | % Sn |
| IX | Ethylene Glycol 1.0 | 0.43 | 0.84 | 13.7 |
| X | Ethylene Glycol 1.5 | 0.81 | 0.80 | 13.4 |
| XI | Ethylene Glycol 2.0 | 1.18 | 0.93 | 13.6 |
| XII | Propylene Glycol 1.0 | 0.87 | 1.16 | |
| XIII | 1,4-Butylene Glycol 1.0 | 1.27 | 1.27 | |

EXAMPLES XIV and XV

Two moles (524 g) dibutyl thiomalate and one mole dimethyltin dichloride (220 g) were mixed and two moles aqueous 10% sodium hydroxide solution then added slowly. The reaction temperature was held at 60° C for one half hour after the addition of the sodium hydroxide solution was complete. The final pH of the reaction mixture was 5.7.

The mixture was separated easily at 60° C in a separatory funnel. The organic portion, the lower layer, was dried and vacuum stripped at 20 to 25 mm of mercury and to a maximum pot temperature of 60° C. When all of the water had been removed, the product was filtered, giving a clear, light product identified as dimethyltin bis-(dibutyl thiomalate).

The dimethyltin bis (dibutyl thiomalate) was then mixed with 1,4-butylene glycol or neopentylene glycol in the proportion of one mole alkylene glycol per mole of dimethyltin bis (dibutyl thiomalate) and the mixture then heated for three hours at from 120° to 125° C. At the conclusion of this reaction time, the butanol liberated in the course of transesterification with the alkylene glycol was removed by vacuum-stripping to 130° C maximum pot temperature.

As the reaction proceeded the initially immiscible alkylene glycol dissolved in the reaction mixture, and the product, after the removal of butanol, remained clear. In the course of vacuum stripping, unreacted 1,4-butylene glycol and neopentylene glycol was also distilled off, and consequently the transesterification product was considered to be free of both unreacted alkylene glycol and butanol.

Two runs were made under these conditions with the following results:

TABLE IV

| Example No. | Glycol Charged Moles/Mole Organotin | Butanol Distilled Moles/Mole Of | |
|---|---|---|---|
| | | Dimethyltin Bis-(Butyl Thiomalate) | Glycol Reactant |
| XIV | 1,4-Butylene glycol | 1.74 | 1.74 |
| XV | Neopentylene glycol | 1.0 | 1.17 |

The data for Examples I to XV show that the maximum quantity of alkylene glycol that reacts in this transesterification reaction is about two moles of glycol per mole of dialkyltin bis-(dibutyl thiomalate), and the maximum yield of butanol liberated in the transesterification is about 1.8 moles per mole of glycol reactant. This establishes that the glycol is reacting both as a monofunctional reagent to introduce the hydroxyalkyl group HOR (for example, 2-hydroxyethyl when ethylene glycol is used) as in Formula II above, and as a bifunctional reagent to introduce the bivalent alkylene group by displacement of two butyl groups linked either to another carboxylic acid group of the same thiomalate group or carboxylic groups of different thiomalate groups, as in Formulae III, IV, V and VI, above.

The appearance of the characteristic hydroxyl group frequency in the infra-red absorption spectra of all of the above transesterification products confirms the presence of hydroxyalkyl groups.

The data also shows that the compounds in accordance with the invention resulting from transesterification of dialkyltin bis-(alkyl thiomalate) with alkylene glycol are best represented as mixtures of compounds with the structural Formulae II, III, IV, V and VI, in which the first three predominate at relatively low glycol: organotin thiomalate ratios, and the last three at higher glycol: organotin thiomalate ratios.

EXAMPLE XVI

One mole of ethylene glycol, 2.5 moles of thiomalic acid, and 3.5 moles of n-butanol were reacted in a reaction vessel equipped with a reflux condenser and a water trap. p-Toluene sulphonic acid 3.5 g was used as an esterification catalyst. In the course of the reaction 94 g of aqueous phase was covered in the water trap and on vacuum-stripping 9 g of distillate was obtained, with a refractive index of 1.4076, corresponding roughly to a mixture of butanol (refractive index 1.3993) and ethylene glycol (refractive index 1.4318). The reaction product amounted to 595 g, and had the following properties:

| | |
|---|---|
| Density 25° C | 1.108 |
| Refractive Index | 1.4717 |
| Gardner Viscosity | A-4 |

| | |
|---|---|
| Perccent SH | 13.28 |

One mole of dibutyltin oxide (249 g) and two SH-equivalents of the above butyl-ethylene glycol thiomalate (498 g) were mixed and heated at 120° C with stirring and vacuum-stripping in a three-neck flask until the dibutyltin oxide had disappeared. This required one half hour, and yielded 35 ml of distillate, that separated into two layers and contained both water and n-butanol and a cloudy ethylene glycol-containing liquid product. The residue product was essentially free of butanol and was considered to be dibutyltin-bis-(butyl-ethylene glycol thiomalate). The tin content was 16.2%. Comparative storage tests were carried out with this product and conventional organotin stabilizers at 22° to 26° C. (room temperature), as follows:

| Product | Time to appearance of precipitate |
|---|---|
| Example XVI | None after 360 days |
| Di-n-butyltin-bis (isoctyl thioglycolate) | 20 days |
| Same with 5% added calcium 2-ethyl hexoate | 40 days |
| Same with 5% added di-isoamyl phosphate | 40 days |

This remarkable freedom from precipitation over a long storage time represents a solution of a problem of long standing and an important commercial advantage.

EXAMPLE XVII

In a four-necked flask equipped with a condenser, stirrer, thermometer, and chilled receiver there was charged 2 moles of dimethyl thiomalate, 300 cc of benzene and 1 mole of ethylene glycol. The reaction mixture was heated to 100°-125° C with vigorous stirring and distillation until 71 cc of methanol was obtained, thus indicating that the transesterification was practically complete. The resulting reaction mixture was cooled, and there was then added to it 2 moles of the dibutyltin monodimethyl thiomalate, which had been prepared by reacting 2 moles of dibutyltin oxide with 2 moles of dimethyl thiomalate at 110°-125° C. The reaction mixture was refluxed for one hour with stirring, and a vacuum was applied to remove the solvent. A viscous yellow-colored product was obtained. This product analyzed as containing 20.9% Sn, 11.7% S, vs theoretical 21.44% Sn, 11.53% S.

This product had the formula:

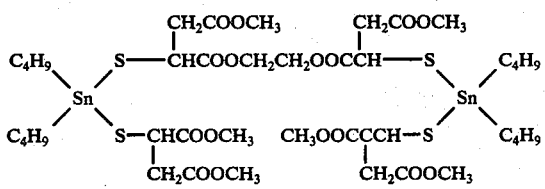

EXAMPLE XVIII

An organotin thiomalate ester was prepared in the same fashion as described in Example XVI but using dibutyl thiomalate in place of dimethyl thiomalate. The product was a pale yellowish viscous liquid, which analyzed 16.6% Sn, 8.9% S, vs theoretical 17.4% Sn, 9.40% S.

This product had the formula:

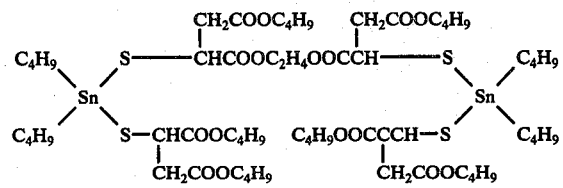

EXAMPLE XIX

The reaction described in Example XVIII was repeated with the dibutyl thiomalate ester, but in place of dibutyltin oxide, dioctyltin oxide was used. The end product was a yellowish viscous liquid which had the approximate formula:

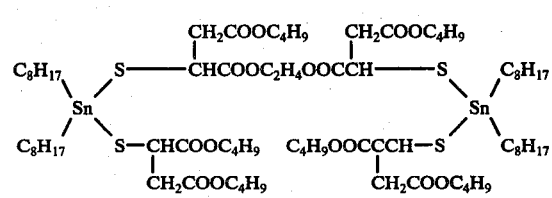

EXAMPLE XX

The procedure of Example XVIII was followed replacing ethylene glycol with propylene glycol. The product obtained corresponded to the formula:

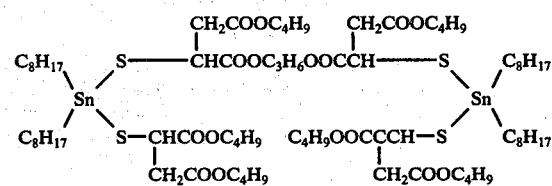

EXAMPLE XXI

The procedure of Example XVIII was repeated using dioctyltin oxide in place of dibutyltin oxide.

EXAMPLE XXII

Freshly prepared dibutyl thiomalate (265 g of about 96% assay, 1 mole) containing 0.75 g toluene sulfonic acid was mixed with neopentyl glycol (52 g, 0.5 mole) and 100 ml benzene. The mixture was stirred and heated under reflux for 7½ hours (pot temperature 116° C) and then vacuum-stripped to 125° C pot temperature and 3 mm to remove benzene and butanol produced by transesterification. The stripped product was stirred one hour at 100° C with 15 g of powdered decolorizing carbon and filtered, to give 298 g neopentylene bis (butyl thiomalate) having density 1.076 at 25° C, $n_d^{25°}$ 1.4455 and 11.6% SH; molecular refractivity calculated from the observed density and refractive index 118.8.

The product accordingly has been designated by the formula:

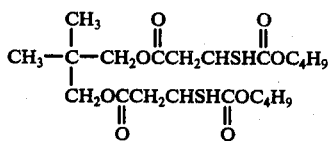

for which calculated % SH is 13.3, and molecular refractivity 116.7.

A 48 g portion of this neopentylene bis-(butyl thiomalate) was reacted at 135° C for 45 minutes with 100 g of a 1:1 molar ratio reaction product of dibutylthiomalate with di-n-butyltin oxide.

The resulting dibutyltin neopentylene bis-(butyl thiomalate) has been designated by the formula:

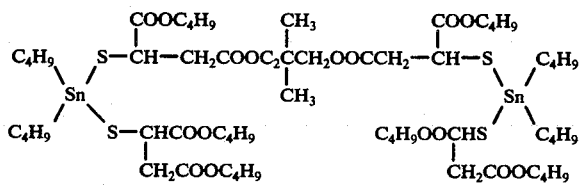

EXAMPLE XXIII

Dibutyl thiomalate 400 g was warmed to 35° C and stirred, while first 14.4 g monobutyltin oxide and then 164.8 g of dibutyltin oxide were added.

The mixture was heated to 110° C during two hours, while most of the oxides dissolved. Water pump vacuum was applied, and heating continued until the reaction mixture reached 120° C to complete removal of reaction water.

To the above dibutyltin-monobutyltin thiomalate was added 12 g ethylene glycol, and heating was continued for three hours at 120°–125° C with stirring. Finally, vacuum was again applied to 130° C maximum to distill out 20 g butanol. Filtration of the residue product gave 528 g of pale yellow dibutyltin-monobutyltin butyl ethylene thiomalate. Analysis by atomic absorption spectroscopy showed that the product contained 16.6% Sn.

EXAMPLE XXIV

Example XVIII was repeated using one mole of ethylene glycol transesterified derivative with two moles dibutyl thiomalate. The resulting product was reacted with one mole of the 1:1 molar reaction product of dibutyltin oxide with dibutyl thiomalate. The resulting product was reacted further with one-half mole dibutyltin bis-(mono methyl maleate) and with one-half mole of dibutyltin bis-(dibutyl thiomalate). The resulting product was a pale yellow viscous liquid which had the following approximate structure:

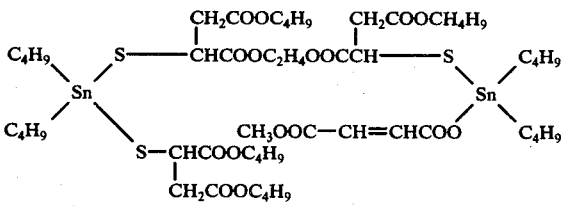

EXAMPLE XXV

One mole ethylene glycol, 2.5 moles thiomalic acid, and 3.5 moles n-butanol were reacted under a reflux fitted with water trap. p-Toluenesulfonic acid 3.5 g was used as esterification catalyst. The reaction gave 94 grams aqueous phase in the trap, 9 grams distillate on vacuum stripping with refractive index 1.4076 (butanol RI = 1.3993 and ethylene glycol = 1.4318) and 595 grams of product with the following properties:

| | |
|---|---|
| Density 25° C | 1.108 |
| Refractive Index 25° C | 1.4714 |
| Gardner Viscosity 25° C | A-4 |
| Percent SH | 13.28 |
| Molecular Refractivity (Calculated from density and R$_1$) | 63.1 |

The infrared spectrum of this product showed a characteristic hydroxyl absorption band.

Consistent with these properties, the product is designated butyl ethylene thiomalate for which calculated % SH is 13.25 and molecular refractivity is 58.8, and the formula assigned is

Three di-n-octyltin stabilizers (A,B,C) were prepared from this product by reacting the thiomalate with different proportions of di-n-octyltin oxide. In each instance, the thiomalate was warmed to 55° C, di-n-octyltin oxide added with stirring during a half-hour period, and water aspirator vacuum applied while warming to 80° C, then holding at 80° C for 2 hours to complete the removal of by-product water.

The resulting pale yellow liquid products were filtered with suction to remove very small traces of solid impurities introduced along with the di-n-octyltin oxide. Details are tabulated in Table V.

TABLE V

| Example | A | B | C |
|---|---|---|---|
| Butylethylene thiomalate | 62.5 g | 55 g | 45 g |
| Di-n-octyltin oxide | 37.5 g | 45 g | 55 g |
| Yield of di-n-octyltin salt | 94 g | 92 g | 89 g |
| % Sn (atomic absorption) | 12.25 | 14.9 | 17.7 |
| %S (iodimetric) | 8.1 | 7.2 | 5.9 |
| Sulfur/tin molar ratio | 2.4 | 1.8 | 1.2 |

EXAMPLE XXVI a. Dibutyl thiomalate preparation:

This ester was obtained in 96.7% yield by reaction of 6000 g thiomalic acid, 9000 g butanol, 166 ml benzene, and 66.6 g p-toluene sulfonic acid catalyst. Properties of the dibutyl thiomalate were as follows:

| | |
|---|---|
| Refractive Index | 1.4570 |
| Density | 1.015 |
| Viscosity (Gardner) | less than A-5 |

| | |
|---|---|
| -continued | |
| Percent SH (Theoretical %SH = 12.6) | 12.25, 12.34 |
| Weight Yield | 10.545 g |
| Weight recovered butanol | 3040 g | b. Transesterification:

Two moles dibutyl thiomalate, 1 mole ethylene glycol, and 3 g tetrabutyl titanate catalyst were stirred and heated for 3 hours at 125° C. Vacuum was then applied, and volatiles stripped off to 135° C and 18 mm, to give butyl ethylene thiomalate having the following properties:

| | |
|---|---|
| Weight | 503 g |
| Refractive Index | 1.4632 |
| Density | 1.063 |
| Viscosity (Gardner) | A-4 |
| Percent SH | 12.42 |

Four monobutyltin stabilizers were prepared from this butylethylene thiomalate by reaction with 44% aqueous monobutyltin trichloride and 15% aqueous sodium hydroxide at 75°-80° C. The products were isolated by extraction of the milky reaction mixtures with cyclohexane, filtration, and evaporation of the extracts. Quantities of reagents used (on dry basis) and products obtained are shown in Table VI.

TABLE VI

| | A | B | C | D |
|---|---|---|---|---|
| Butylethylene thiomalate | 80 g | 72 g | 72 g | 72 g |
| Butyltin trichloride | 28.2 g | 28.2 g | 28.2 g | 28.2 g |
| Sodium hydroxide | 12.0 g | 12.0 g | 11.4 g | 10.8 g |
| Weight monobutyltin butylethylene thiomalate | 91 g | 80 g | 81 g | 81 g |
| % Sn (atomic absorption) | 12.0 g | 12.9 g | 12.8 g | 12.8 g |
| % S (iodometric) | 9.6 g | 9.5 | 9.5 | 9.4 |
| % Cl | 0.2 | 0.3 | 0.6 | 1.1 |

EXAMPLE XXVII

Transesterifications of dibutyl thiomalate with ethylene glycol and various catalysts were run on a scale of about one mole (270 g of about 96% pure) dibutyl thiomalate, 0.5 mole (32 g) ethylene glycol, and catalyst under the conditions shown in Table VII below.

TABLE VII

| | | | Butyl Ethylene Thiomalate | | |
|---|---|---|---|---|---|
| Catalyst g. | Time Hrs. | Final Temp ° C | Yield g. | R.I. 25° C. | % SH |
| A Sodium Methoxide 0.7 | 3 | 122 | 259 | 1.4580 | 8.03 |
| B Butyl titanate 1.5 | 4 | 135 | 268.5 | 1.4569 | 12.3 |
| C Dibutyltin oxide 1.5 | 4 | 165 | 252 | 1.4579 | 12.2 |
| D p-Toluenesulfonic acid 1.5 | 4 | 160 | 270 | 1.4582 | 12.3 |

Dibutyltin stabilizers were prepared from the above butyl ethylene thiomalates as follows:

Dibutyl thiomalate 140 grams (93% assay) was warmed to 90° C and dibutyltin oxide 125 grams was added slowly with stirring and continued heating. The dibutyltin oxide had dissolved by the time the mixture reached 130° C to give dibutyltin mono (dibutyl thiomalate) a viscous liquid.

A 50 g portion of each of the above preparations of butyl ethylene thiomalate was warmed to 125° C, and 106 g of dibutyltin mono (dibutyl thiomalate) prepared as above was added with stirring, to give a homogeneous liquid product represented by the formula in Example XVIII.

EXAMPLES XXVIII TO XXXIV

Additional glycol alkyl thiomalates were prepared by direct esterification following the general procedure of Example XXV using 375 g (2.5 moles) thiomalic acid, except for increased catalyst use (6 g p-TSA) and temperature held to 125° C maximum by adding hexane as needed. The reaction conditions and results are shown in Table VIII. The yield refers to stripped product, after heating under vacuum to 135° C.

TABLE VIII

| Example No. | Glycol | grams | Alcohol | grams | Yield g. | %SH Theor. | %SH Actual |
|---|---|---|---|---|---|---|---|
| XXVIII | Neopentylglycol | 104 | Isobutyl alcohol | 259 | 643 | 12.83 | 12.3 |
| XXIX | Diethylene glycol | 106 | Isoborneol | 539 | 879 | 9.39 | 9.0 |
| XXX | Ethylene glycol | 62 | n-Hexanol | 357 | 737 | 11.19 | 10.4 |
| XXXI | Ethylene glycol | 62 | 2-Ethylhexanol | 455 | 797 | 10.35 | 10.0 |
| XXXII | Cyclohexane-dimethanol-1,4 | 144 | n-Propyl alcohol | 210 | 627 | 13.16 | 12.5 |
| XXXIII | Ethylene glycol | 93 | 2-Phenylethanol | 305 | 674 | 12.24 | 11.9 |
| XXXIV | Propylene glycol | 114 | n-Dodecyl alcohol | 465 | 857 | 9.63 | 9.1 |

The odor characteristics of representative organotin thiomalate esters in accordance with the invention were evaluated by the following tests:

TEST A

A mixture of 200 g polyvinyl chloride homopolymer and 5 g of the organotin thiomalate ester being tested was blended five times for 20 seconds in an Osterizer high speed mixer, with 10 second rest intervals. The resulting blend was placed in a glass jar fitted with a metal screw cap, and heated for 30 minutes in an air circulating oven at 150° C., the closed glass jar was then allowed to cool to room temperature and sniff-tested the next day.

The organotin thiomalate esters set forth below were tested in this manner, and were found to give essentially odorless blends:

Example XVI; Dibutyltin bis-(butyl ethylene thiomalate)

Example I; Dimethyltin bis-(butyl ethylene thiomalate)

The following organotin compounds not of the invention gave blends with an odor considered characteristic of isooctyl thioglycolate:

Commercial Butyltin stabilizer, dibutylin bis(isooctyl thioglycolate)

Commercial Octyltin stabilizer, di-n-octyltin bis-(isooctyl thioglycolate)

Commercial low odor organotin stabilizer of unknown constitution

The superiority of the organotin thiomalate esters of the invention is evident from the results of this test, which measures the tendency of the plastic to release odors during compounding and processing.

TEST B

A mixture of 100 g polyvinyl chloride homopolymer, 2 g acrylic process aid, 0.5 g Wax E lubricant and 3 g of the organotin stabilizer being tested was fluxed on a two role mill at about 330° F for five minutes and sheeted off. The sheet was cut into strips measuring about 2½ by 1 inches and the maximum possible quantity of these strips (65 or more of plastic) placed in an 8 oz. glass jar fitted with a metal screw cap. The closed jars were kept in an air circulating oven at 60° C for 60 days, allowed to cool to room temperature and sniffed the next day.

The following organotin thiomalate esters were tested in this way and found to give odorless plastics.

Example IX; Di-n-octyltin butylethylene thiomalate

Example X; Di-n-octyltin butylethylene thiomalate

Example XI; Di-n-octyltin butylethylene thiomalate

Example XII; Di-n-octyltin butylpropylene thiomalate

Example XIII; Di-n-octyltin butyl 1,4-butylene thiomalate

The following organotin compound not of the invention in this test gave a plastic with a recognizable mercaptoester odor:

Commercial octyltin stabilizer, di-n-octyltin di-(isooctyl thioglycolate).

The superiority of organotin alkyl glycol thiomalate esters of the invention with different kinds and proportions of glycol is evident from the results of this test, which measures the tendency of the plastic to release odors during storage and use.

The organotin thiomalate ester halides of the invention can be used as stabilizers with any polyvinyl chloride resin. The term "polyvinyl chloride" as used herein is inclusive of any polymer formed at least in part of the recurring group

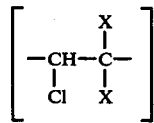

and having a chlorine content in excess of 40%. In this group, the X groups can each be either hydrogen or chlorine. In polyvinyl chloride homopolymers, each of the X groups is hydrogen. Thus, the term includes not only polyvinyl chloride homopolymers but also after-chlorinated polyvinyl chlorides such as those disclosed in British Pat. No. 893,288 and also copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene, propylene, and ethylene. The invention also is applicable to mixtures of polyvinyl chloride in a major proportion with other synthetic resins such as chlorinated polyethylene or a copolymer of acrylonitrile, butadiene and styrene. Among the polyvinyl chlorides which can be stabilized are the uniaxially-stretch oriented polyvinyl chlorides described in U.S. Pat. No. 2,984,593 to Isaksem et al, that is, syndiotactic polyvinyl chloride, as well as atactic and isotactic polyvinyl chlorides.

The organotin mercaptodicarboxylate esters of this invention, both with and without supplementary stabilizers, are excellent stabilizers for both plasticized and unplasticized polyvinyl chloride resins. When plasticizers are to be employed, they may be incorporated into the polyvinyl chloride resins in accordance with conventional means. The conventional plasticizers can be used, such as dioctyl phthalate, dioctyl sebacate and tricresyl phosphate. Where a plasticizer is employed, it can be used in an amount within the range from 0 to 100 parts by weight of the resin.

Particularly useful plasticizers are the epoxy higher fatty acid esters having from about twenty to about one hundred fifty carbon atoms. Such esters will initially have had unsaturation in the alcohol or acid portion of the molecule, which is taken up by the formation of the epoxy group.

Typical unsaturated acids are oleic, linoleic, linolenic, erucic, ricinoleic and brassidic acids, and these may be esterified with organic monohydric or polyhydric alcohols, the total number of carbon atoms of the acid and the alcohol being within the range stated. Typical monohydric alcohols include butyl alcohol, 2-ethylhexyl alcohol, lauryl alcohol, isooctyl alcohol, stearyl alcohol, and oleyl alcohol. The octyl alcohols are preferred. Typical polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid. Also useful are the epoxidized mixtures of higher fatty acid esters found in naturally-occurring oils such as epoxidized soybean oil, epoxidized olive oil, epoxidized cottonseed oil, epoxidized tall oil fatty acid esters, epoxidized linseed oil and epoxidized tallow. Of these, epoxidized soybean oil is preferred.

The alcohol can contain the epoxy group and have a long or short chain, and the acid can have a short or long chain, such as epoxy stearyl acetate, epoxy stearyl stearate, glycidyl stearate, and polymerized glycidyl methacrylate.

A small amount, usually not more than 1.5%, of a parting agent or lubricant, also can be included. Typical parting agents are the higher aliphatic acids, and salts having 12 to 24 carbon atoms, such as stearic acid, lauric acid, palmitic acid and myristic acid, lithium stearate and calcium palmitate, mineral lubricating oils, polyvinyl stearate, polyethylene and paraffin wax.

Impact modifiers, for improving the toughness or impact-resistance of unplasticized resins, can also be added to the resin compositions stabilized by the present invention in minor amounts of usually not more than 10%. Examples of such impact modifiers include chlorinated polyethylene, ABS polymers, and polyacrylate butadiene graft copolymers.

The organotin thiomalate esters of the invention are employed in an amount sufficient to impart the desired resistance to heat deterioration at working temperatures of 350° F and above. The longer the time and the more rigorous the conditions to which the resin will be subjected during working and mixing, the greater will be the amount required. Generally, as little as 0.25% total of the organotin thiomalate ester by weight of the resin will improve resistance to heat deterioration. There is no critical upper limit on the amount, but amounts above about 10% by weight of the resin do not give an increase in stabilizing effectiveness that is commensurate with the additional amount employed. Preferably, the amount is from about 0.5 to about 5% by weight of the resin.

The organotin thiomalate esters of the invention are extremely effective when used alone, but they can be employed together with other polyvinyl chloride resin stabilizers, including non-mercaptide organotin compounds, particularly organotin maleate half-esters, if special efforts are desired. The organotin thiomalate esters of the invention in this event will be the major stabilizer, and the additional stabilizer will supplement the stabilizing action of the former, the amount of the organotin thiomalate ester being within the range from about 0.25 to about 10 parts by weight per 100 parts of the resin, and the additional stabilizer being in the amount of from about 0.05 to about 10 parts of the resin.

Among the additional metallic stabilizers are included polyvalent metal salts of medium and of high molecular weight fatty acids and phenols, with metals such as calcium, tin, barium, zinc, magnesium, and strontium. The non-metallic stabilizers include phosphites, epoxy compounds, phenolic antioxidants, polyhydric alcohols, and the like. Epoxy compounds are especially useful, and typical compounds are described in U.S. Pat. No. 2,997,454.

The stabilizer compositions of this invention can be formulated for marketing by mixing the organotin thiomalate ester with an inert diluent or with any liquid lubricant or plasticizer in suitable concentrations, ready to be added to the resin composition to give an appropriate stabilizer and lubricant or plasticizer concentration in the resin. Other stabilizers and stabilizer adjuncts can be incorporated as well.

The preparation of the polyvinyl chloride resin composition is easily accomplished by conventional procedures. The selected stabilizer composition is formed, as described above, and then is blended with the polyvinyl chloride resins, or alternatively, the components are blended individually in the resin, using, for instance, a two or three roll mill, at a temperature at which the mix is fluid and thorough blending facilitated, milling the resin composition including any plasticizer at from 250° to 375° F for a time sufficient to form a homogeneous mass, five minutes, usually. After the mass is uniform, it is sheeted off in the usual way.

For the commercial processing of rigid polyvinyl chloride, the stabilizer composition is conveniently mixed with all or a portion of the polymer to be stabilized with vigorous agitation, under such conditions to time and temperature that the stabilizer is sufficiently imbibed by the polymer to produce a dry, free-flowing powder. The well-known Henschel mixer is well suited to this procedure.

The following Examples in the opinion of the inventor represent preferred embodiments of polyvinyl chloride resin compositions incorporating organotin thiodicarboxylic acid esters in accordance with the invention as stabilizers therefor.

EXAMPLES 1 to 3

The effectiveness as stabilizers for polyvinyl chloride resins of a number of organotin thiomalate esters in accordance with the invention was evaluated using a 205° C (400° F) oven heat stability test. The polyvinyl chloride resin test formulation employed was as follows:

| Component | Parts By Weight |
|---|---|
| Vinyl chloride homopolymer (Diamond 40) | 100 |
| Acrylic impact modifier (Kureha BTA-3) | 10 |
| Acrylic processing aid (Acryloid K-120N) | 3 |
| Lubricant (Wax E) | 0.3 |
| Stabilizer | 2 |

The composition was milled on a two-roll mill at approximately 375° F. After three minutes of mixing, the composition was sheeted off, and the sheets cut into strips, which were then placed in an oven heated at 205° C, and held there for up to 2 hours, or less, if the strips turned black before this time. Samples were removed from the strips and affixed to cards at 5-minute intervals, to evaluate the progressive heat-deterioration of the resin.

The following organotin thiomalate esters were subjected to this test:
  a. dimethyltin (butyl ethylene thiomalate) of Example I, Run No. 1.
  b. dibutyltin (butyl ethylene thiomalate) of Example I, Run No. 4.
  c. dimethyltin (butyl neopentylene thiomalate) of Example XV.

The degree of heat degradation was evaluated by the amount of color formed, that is, the extent of discoloration, relative to Control A, a test formulation containing dimethyltin bis-(isooctyl thioglycolate) (18.9% tin), and Control B, dimethyltin bis (di-n-butyl thiomalate).

The scale used to characterize the amount of color formation is set forth below as Table IX. The scale covers the color range from colorless through yellow and orange to reddish brown, and ranges numerically from 0-colorless to 9-brown-black, as follows:

TABLE IX

| | |
|---|---|
| 0 | Clear and colorless |
| 1 | Touch of yellow |
| 2 | Very pale yellow |
| 3 | Pale yellow |
| 4 | Yellow |
| 5 | Yellow-brown edges |
| 6 | Light orange brown |
| 7 | Orange brown |
| 8 | Reddish brown |
| 9 | Brown-black |

The appearance of the samples evaluated in accordance with this test is set forth in Table X.

TABLE X

| Minutes 400° F | Ex. 1 | Ex. 2 | Ex. 3 | Control A | Control B |
|---|---|---|---|---|---|
| 0 | 0 | 0 | 0 | 0 | 0 |
| 5 | 0 | 0 | 0 | 0 | 0 |
| 10 | 0 | 0 | 0 | 1 | 1 |
| 15 | 1 | 0 | 1 | 4 | 4 |
| 20 | 4 | 3 | 3 | 6 | 6 |
| 25 | 6 | 4 | 7 | 8 | 9 |
| 30 | 9 | 7 | 9 | 9 | 9 |
| 35 | 9 | 9 | 9 | 9 | 9 |

During the milling of the samples a strong mercapto-ester odor was produced from Control A and a hydrogen sulfide odor from Control B, but no sulfur compound odor was noted from Examples 1, 2, and 3. The heat stability of Examples 1, 2, and 3 is clearly superior to Controls A and B.

EXAMPLES 4 to 6

In these examples, a stabilizer of the invention, dibutyltinmonobutyltin ethylene thiomalate of Example XXIII, was compared to dibutyltin bis (isooctylthioglycolate) at three stabilizer use levels, as indicated in Table XI in parts per 100 parts of resin, in the following:

| Test formulation: | Parts by Weight |
| --- | --- |
| Vinyl chloride homopolymer (Diamond 40) | 100 |
| Acrylic impact modifier (Kureha BTA-3) | 10 |
| Lubricants: | |
| Wax E montan wax ester | 0.5 |
| Glycerol monostearate | 0.5 |
| AC 629 (low molecular weight polyethylene) | 0.2 |

The compositions were milled on a two-roll mill at about 375° F. After three minutes of mixing, the compositions were sheeted off, and the sheets cut into strips, which were placed in an oven heated at 375° F and at 400° F. The following results were obtained:

TABLE XI

| 375° F Minutes | Example 4 0.3 part | Example 5 0.75 part | Example 6 1.5 parts | Dibutyltin bis (isooctyl thioglycolate) | | |
| --- | --- | --- | --- | --- | --- | --- |
| | | | | 0.3 part | 0.75 part | 1.5 parts |
| 0 | 0 | 0 | 0 | 0 | 0 | 0 |
| 5 | 0 | 0 | 0 | 2 | 1 | 0 |
| 10 | 1 | 0 | 0 | 4 | 1 | 0 |
| 15 | 3 | 0 | 0 | 5 | 2 | 1 |
| 20 | 6 | 1 | 0 | 8 | 3 | 1 |
| 25 | 7 | 1 | 0 | 8 | 4 | 2 |
| 30 | 7 | 2 | 0 | 8 | 4 | 2 |
| 35 | 7 | 3 | 1 | 8 | 5 | 3 |
| 40 | 7 | 4 | 1 | 8 | 5 | 3 |

| 400° F (Minutes) | Example 4 0.3 part | Example 5 0.75 part | Example 6 1.5 part | Dibutyltin bis (isooctyl thioglycolate) | | |
| --- | --- | --- | --- | --- | --- | --- |
| | | | | 0.3 part | 0.75 part | 1.5 parts |
| 0 | 0 | 0 | 0 | 0 | 0 | 0 |
| 5 | 2 | 0 | 0 | 4 | 2 | 1 |
| 10 | 7 | 1 | 1 | 8 | 3 | 2 |
| 15 | 8 | 3 | 1 | 9 | 5 | 3 |
| 20 | 9 | 5 | 2 | 9 | 8 | 4 |
| 25 | 9 | 8 | 3 | — | 9 | 5 |
| 30 | — | 9 | 4 | — | — | 8 |

The test results show that the 16.6% tin content stabilizer of this invention is remarkably superior to the 18.0% tin content stabilizer that has long been considered the standard of the industry. In spite of the lower tin content, 0.75 part of the stabilizer in Example 5 gives better stabilization than 1.5 parts of dibutyltin bis-(isooctyl thioglycolate). In addition, the samples of Examples 4, 5, and 6 were free of the objectionable mercaptoester odor that characterized the samples containing dibutyltin bis-(isooctyl thioglycolate).

EXAMPLES 7 to 10

Formulations were prepared employing the reaction products of dibutyltin mono (dibutyltiomalate) and butyl ethylene thiomalate of Examples XXVII A, B, C, and D in the following formulation.

| Formulation: | Parts by weight |
| --- | --- |
| Polyvinyl chloride homopolymer (Borden VC-95) | 100 |
| Acrylic impact modifier | 10 |
| Acrylic process aid | 3 |
| Wax E lubricant | 0.3 |
| Stabilizer | 2.0 |

The formulations were milled, on a two-roll mill at about 375° F. After 3 minutes of mixing, the compositions were sheeted off, and the sheets cut into strips, which were placed in an oven heated at 400° F. The following results were obtained:

TABLE XII

| 400° F Minutes | Example 7 (Ex XXVIIA) | Example 8 (Ex XXVIIB) | Example 9 (Ex XXVIIC) | Example 10 (Ex XXVIID) |
| --- | --- | --- | --- | --- |
| 0 | 0 | 0 | 0 | 0 |
| 5 | 0 | 0 | 0 | 0 |
| 10 | 0 | 0 | 0 | 0 |
| 15 | 3 | 1 | 3 | 1 |
| 20 | 6 | 1 | 6 | 4 |
| 25 | 8 | 6 | 8 | 7 |

All samples provided good early color control, and acceptable long term heat stability.

EXAMPLE 11

In this example, the butyltin butylethylene thiomalate product of Example III was compared to the dibutyltin thiomalic acid of Weinberg U.S. Pat. No. 2,832,752 in the following formulation:

| | Parts by Weight |
| --- | --- |
| Polyvinyl chloride homopolymer (Diamond 40) | 100 |
| Calcium stearate (lubricant) | 1 |
| Acrylic process aid | 2 |
| Stabilizer | 2.0 |

The formulations were milled, on a two-roll mill at about 375° F. After 3 minutes of mixing, the compositions were sheeted off, and the sheets cut into strips, which were placed in ovens heated at 375° F and at 400° F. The following results were obtained:

TABLE XIII

| | Oven test 375° F. | | Oven test 400° F. | |
|---|---|---|---|---|
| Minutes | Example 11 15.8% Sn | Dibutyltin bis (thiomalic acid) 18.9% Sn | Example 11 15.8% Sn | Dibutyltin bis (thiomalic acid) 18.9% Sn |
| 0 | 0 | 0 | 0 | 0 |
| 5 | 0 | 0 | 0 | 1 |
| 10 | 0 | 1 | 0 | 3 |
| 15 | 0 | 2 | 1 | 5 |
| 20 | 1 | 2 | 2 | 6 |
| 25 | 1 | 3 | 7 | 7 |
| 30 | 1 | 3 | 9 | 9 |
| 35 | 1 | 4 | — | — |
| 40 | 1 | 4 | — | — |

Clearly the product of Example 11 provides superior stabilization in spite of a lower tin content.

EXAMPLES 12 to 17

The Di-n-octyltin derivatives of butyl glycol thiomalates of Examples X, XII, XIII, XXVA, XXVB, and XXVC were compared in the following resin formulation:

| | Parts by Weight |
|---|---|
| Diamond 40 polyvinyl chloride homopolymer | 100 |
| Acrylic impact modifier | 10 |
| Acrylic process aid | 2 |
| Glycerlymonoricinoleate lubricant | 0.5 |
| Stabilizer | 1.5 |

The formulations were milled, on a two-roll mill at about 375° F. After 3 minutes of mixing, the compositions were sheeted off, and the sheets cut into strips, which were placed in an oven heated at 375° F and at 400° F. The following results were obtained:

TABLE XIV

| 400° F Minutes | Control Di-n-octyltinbis (isooctylthioglycolate) | Example 12 Ex. X | Example 13 Ex. XII | Example 14 Ex. XIII | Example 15 Ex. XXVA | Example 16 Ex. XXVB | Example 17 Ex. XXVC |
|---|---|---|---|---|---|---|---|
| 0 | 0 | 0 | 0 | 0 | 0 | 0 | 0 |
| 5 | 1 | 0 | 0 | 0 | 1 | 0 | 1 |
| 10 | 3 | 2 | 3 | 3 | 3 | 2 | 2 |
| 15 | 4 | 4 | 4 | 4 | 4 | 4 | 3 |
| 20 | 5 | 6 | 6 | 6 | 5 | 5 | 5 |
| 25 | 9 | 9 | 8 | 9 | 8 | 8 | 6 |
| 30 | — | — | 9 | — | 8 | 9 | 8 |
| 35 | — | — | — | — | 9 | — | — |

The dioctyl tin bis-(isooctyl thioglycolate) exhibited a pronounced mercaptoester odor while being milled and also on subsequent aging of 65 g plastic in an 8 oz. jar at 60° C, while the other samples of Examples 12 to 17 were free or odor. The stabilizers of Examples 12 to 17 all have lower tin contents, but provide either equivalent or better heat stability than the dioctyltin bis-(isooctyl thioglycolate).

| | Parts by Weight |
|---|---|
| Diamond 40 polyvinyl chloride homopolymer | 100 |
| Acrylic impact modifier | 10 |
| Acrylic process aid | 3 |
| Wax E lubricant | 0.3 |
| Stabilizer | 2.0 |

TABLE XV

| 400° F Minutes | Dioctyltin bis iso-octyl thioglycolate | Example 15 Ex. XXV A | Example 16 Ex. XXV B | Example 17 Ex. XXV C |
|---|---|---|---|---|
| 0 | 0 | 0 | 0 | 0 |
| 5 | 1 | 1 | 0 | 1 |
| 10 | 3 | 3 | 2 | 2 |
| 15 | 4 | 4 | 4 | 3 |
| 20 | 5 | 5 | 5 | 5 |
| 25 | 9 | 8 | 8 | 6 |
| 30 | — | 8 | 9 | 8 |
| 35 | — | 9 | — | — |

EXAMPLES 18 to 20

The di-n-octyltin butyl glycol thiomalates of Examples IX, X and XI were compared in the following formulation:

| | Parts by Weight |
|---|---|
| Diamond 40 polyvinyl chloride homopolymer | 100 |
| Acrylic impact modifier | 10 |
| Acrylic process aid | 2 |
| Glycerylmonoricinoleate | 0.5 |
| Stabilizer | 1.5 |

The compositions were milled on a two-roll mill at about 375° F. After three minutes of mixing, the compositions were sheeted off and the sheets cut into strips, which were placed in an oven heated at 400° F. The following results were obtained:

TABLE XVI

| 400° F Minutes | Ex. 18 Ex. IX | Ex. 19 Ex. X | Ex. 20 Ex. XI | Di-n-octyltin bis (isooctyl thioglycolate) |
|---|---|---|---|---|
| 0 | 0 | 0 | 0 | 0 |
| 5 | 0 | 0 | 0 | 1 |
| 10 | 2 | 2 | 2 | 3 |
| 15 | 3 | 4 | 4 | 4 |
| 20 | 5 | 6 | 5 | 6 |
| 25 | 9 | 9 | 8 | 8 |
| 30 | — | — | 9 | 9 |

The samples of Examples 18 to 20 had at least equal heat stability to di-n-octyltin bis (isooctyl thioglycolate) in spite of a lower tin content, and also were far superior in oder quality while milling and on aging of milled plastic in jars at 60° C.

EXAMPLES 21 to 25

The dibutyltin butyl ethylene thiomalate of Example XVI was blended with various quantities of mixed dibutyltin-monobutyltin ethylene thiomalate of Example III, to study the effect of the monobutyltin component in the following resin formulation.

|  | Parts by Weight |
|---|---|
| Diamond 40 polyvinyl chloride homopolymer | 100 |
| Acrylic impact modifier | 10 |
| Acrylic process aid | 3 |
| Wax E lubricant | 0.3 |

The compositions were milled on a two-roll mill at about 375° F. After 3 minutes of mixing, the compositions were sheeted off and the sheets cut into strips, which were placed in an oven heated at 400° F. The following results were obtained:

TABLE XVII

| 400° F Minutes | Example 21 Ex. XVI, 2.0 | Example 22 Ex. XVI 1.85 Ex. III 0.15 | Example 23 Ex. XVI, 1.7 Ex. III, 0.3 | Example 24 Ex. XVI, 1.2 Ex. III, 0.8 | Example 25 Ex. XVI, 1.2 Ex. III, 0.8 | Dibutyltin bis isooctyl thioglycolate |
|---|---|---|---|---|---|---|
| 0 | 0 | 0 | 0 | 0 | 0 | 0 |
| 5 | 0 | 0 | 0 | 0 | 0 | 1 |
| 10 | 0 | 0 | 0 | 0 | 1 | 1 |
| 15 | 1 | 1 | 1 | 1 | 1 | 2 |
| 20 | 2 | 2 | 2 | 2 | 3 | 3 |
| 25 | 3 | 3 | 3 | 4 | 4 | 4 |
| 30 | 6 | 6 | 6 | 8 | 8 | 8 |
| 35 | 8 | 8 | 8 | 8 | 8 | 9 |

All samples stabilized with stabilizers of this invention had better initial color control than the dibutyltin bis isooctyl thioglycolate, whether or not a monobutyltin component was present. All formulations containing Examples 21 to 25 were free of mercaptoester odor, while dibutyltin bis isooctyl thioglycolate gave off a noticeable mercaptoester odor during processing, and on subsequent storage in a closed container.

EXAMPLE 26

In this example, the dibytyltin butyl ethylene thiomalate of Example XVI was tested in a flexible plasticized polyvinyl chloride homopolymer composition.

| Formulation: | Parts by Weight |
|---|---|
| Geon 103 EP polyvinyl chloride homopolymer | 100 |
| Dioctyl phthalate | 37 |
| Stabilizer | 1 |

The compositions were milled on a two-roll mill at about 375° F. After 3 minutes of mixing, the compositions were sheeted off and the sheets cut into strips, which were placed in an oven heated at 375° F. The following results were obtained:

TABLE XVIII

| 375° F Minutes | Example 26 Example XVI (16.2% Sn) | Dibutyltin bis isooctyl thioglycolate (18% Sn) |
|---|---|---|
| 0 | Colorless | Colorless |
| 15 | Colorless | Very pale yellow |
| 30 | Colorless | Very pale yellow |
| 45 | Very pale yellow | Pale yellow |
| 60 | Yellow | Yellow |
| 75 | Yellow | Yellow |
| 90 | Yellow | Yellow |
| 105 | Amber | Brown |

TABLE XVIII-continued

| 375° F Minutes | Example 26 Example XVI (16.2% Sn) | Dibutyltin bis isooctyl thioglycolate (18% Sn) |
|---|---|---|
| 120 | Orange | Brown |

At 350° F, both samples remained colorless for 2 hours. The Example 26 samples were free of mercaptoester odor, while the dibutyltin bis isooctyl thioglycolate samples had a pronounced odor during as well as after processing.

EXAMPLE 27

In this Example, rigid PVC was stabilized with di-n-octyltin butyl propylene thiomalate (see Example XII for preparation) above and used together with certain conventional PVC stabilizers.

| Formulation: | Parts by Weight |
|---|---|
| Vinyl chloride - ethylene copolymer (chlorine content 54.8% intrinsic viscosity 0.55 deciliters per gram measured in cyclohexanone at 30° C) | 100 |
| Acrylic impact modifier | 10 |
| Acrylic process aid | 3 |
| Glycerol monostearate lubricant | 0.4 |

| Stabilizers: | Sample A | Sample B | Sample C |
|---|---|---|---|
| Zinc stearate | 0.4 | 0.4 | — |
| Calcium benzoate | 0.3 | 0.3 | — |
| 2,6-di-t-butyl-p-cresol | 0.05 | 0.05 | — |
| Epoxidized soybean oil | 0.5 | 0.5 | — |
| Di-n-octyltin butyl propylene thiomalate (Example XII) | none | 0.5 | 1.0 |

RESULTS:
a) Oven Test 350° F.

| Minutes | Sample A | Sample B | Sample C |
|---|---|---|---|
| 0 | 0 | 0 | 0 |
| 15 | 0 | 0 | 0 |
| 30 | 1 | 0 | 0 |
| 45 | 4 | 0 | 0 |
| 60 | 9 | 1 | 0 |
| 75 | — | 1 | 1 |
| 90 | — | 3 | 1 |
| 105 | — | 6 | 2 |
| 120 | — | 9 | 2 | b) Oven Test 375° F.

| Minutes | Sample A | Sample B | Sample C |
|---|---|---|---|
| 0 | 0 | 0 | 0 |
| 5 | 2 | 0 | 0 |
| 10 | 6 | 1 | 0 |
| 15 | 9 | 1 | 0 |
| 20 | — | 3 | 1 |
| 25 | — | 6 | 1 |
| 30 | — | 9 | 1 |
| 35 | — | — | 2 |
| 40 | — | — | 3 |

The results show excellent stabilization by the di-n-octyltin stabilizer of this invention and significant improvement when added to the conventional calcium-zinc combination. The absence of mercaptoester odor makes economical combinations represented by Sample B practical for clear plastic intended for packaging applications such as bottles.

Having regard to the foregoing disclosure, the following is claimed as inventive and patentable embodiments thereof:

1. An organotin mercapto dicarboxylic acid mixed monohydric and polyhydric alcohol ester having per tin atom one or two alkyl, cycloalkyl or alkylcycloalkyl groups attached to tin through carbon; the alkyl having from 1 to about 12 carbon atoms, the cycloalkyl having from 3 to about 12 carbon atoms, and the alkyl cycloalkyl having from 4 to about 12 carbon atoms; and 2 or 3 mercapto dicarboxylic acid ester groups attached to tin through sulfur, the mercapto dicarboxylic acid having from about four to about 24 carbon atoms, and having at least one esterifying group selected from the group consisting of alkyl, cycloalkyl, and alkylcycloalkyl, the alkyl having from 1 to about 12 carbon atoms, the cycloalkyl having from 3 to about 12 carbon atoms, and the alkyl cycloalkyl having from 4 to about 12 carbon atoms and at least one esterifying group selected from the group consisting of bivalent alkylene, cycloalkylene and alkylenecycloalkyl, the alkylene having from about 2 to about 12 carbon atoms, the cycloalkylene having from 3 to about 12 carbon atoms, and the alkylenecycloalkylene having from 4 to about 12 carbon atoms, each of the two valences of the bivalent alkylene, cycloalkylene and alkylcycloalkylene being linked to groups selected from the group consisting of one hydroxyl and one carboxylic acid group of mercapto dicarboxylic acid; and two carboxylic acid groups of mercapto dicarboxylic acid.

2. An organotin mercapto dicarboxylic acid mixed monohydric and polyhydric alcohol ester according to claim 1, in which the mercapto dicarboxylic acid is thiomalic acid.

3. An organotin mercapto dicarboxylic acid mixed monohydric and polyhydric alcohol ester according to claim 2 having per tin atom one alkyl group linked to tin and three mercapto dicarboxylic acid ester groups esterified with alkyl and alkylene groups.

4. An organotin mercapto dicarboxylic acid mixed monohydric and polyhydric alcohol ester according to claim 3, wherein the alkyl group linked to tin is butyl, the esterifying alkyl group is butyl, and the esterifying alkylene group is ethylene.

5. An organotin mercapto dicarboxylic acid mixed monohydric and polyhydric alcohol ester according to claim 2, having per tin atom two alkyl groups linked to tin, and two mercapto dicarboxylic acid ester groups esterified with alkyl and alkylene groups.

6. An organotin mercapto dicarboxylic acid mixed monohydric and polyhydric alcohol ester according to claim 5, wherein the alkyl group linked to tin is methyl, the esterifying alkyl group is butyl, and the esterifying alkylene group is ethylene.

7. An organotin mercapto dicarboxylic acid mixed monohydric and polyhydric alcohol ester according to claim 5, wherein the alkyl group linked to tin is butyl, the esterifying alkyl group is butyl, and the esterifying alkylene group is ethylene.

8. An organotin mercapto dicarboxylic acid mixed monohydric and polyhydric alcohol ester according to claim 5, wherein the alkyl group linked to tin is butyl, the esterifying alkyl group is butyl, and the esterifying alkylene group is butylene.

9. An organotin mercapto dicarboxylic acid mixed monohydric and polyhydric alcohol ester according to claim 5, wherein the alkyl group linked to tin is butyl, the esterifying alkyl group is butyl, and the esterifying alkylene group is neopentylene.

10. An organotin mercapto dicarboxylic acid mixed monohydric and polyhydric alcohol ester according to claim 5, wherein the alkyl group linked to tin is octyl, the esterifying alkyl group is butyl, and the esterifying alkylene group is ethylene.

11. An organotin mercapto dicarboxylic acid mixed monohydric and polyhydric alcohol ester according to claim 5, wherein the alkyl group linked to tin is octyl, the esterifying alkyl group is butyl, and the esterifying alkylene group is propylene.

12. An organotin mercapto dicarboxylic acid mixed monohydric and polyhydric alcohol ester according to claim 5, wherein the alkyl group linked to tin is octyl, the esterifying alkyl group is butyl, and the esterifying alkylene group is butylene.

13. An organotin mercapto dicarboxylic acid mixed monohydric and polyhydric alcohol ester according to claim 5, wherein the alkyl group linked to tin is methyl, the esterifying alkyl group is butyl, and the esterifying alkylene group is butylene.

14. An organotin mercapto dicarboxylic acid mixed monohydric and polyhydric alcohol ester according to claim 5, wherein the alkyl group linked to tin is methyl, the esterifying alkyl group is butyl, and the esterifying alkylene group is neopentylene.

15. An organotin mercapto dicarboxylic acid ester of claim 1 having per tin atom at least one butyl group linked to tin through carbon.

16. An organotin mercapto dicarboxylic acid ester of claim 1 having per tin atom at least one octyl group linked to tin through carbon.

17. An organotin mercapto dicarboxylic acid ester of claim 1 having per tim atom at least one methyl group linked to tin through carbon.

18. A halogen-containing polymer selected from the group consisting of homopolymers and copolymers of vinyl chloride and chlorinated polymers of vinyl chloride and comprising a stabilizing amount of an organotin mercapto dicarboxylic acid ester of claim 1.

19. The halogen-containing polymer of claim 17 wherein the organotin mercapto dicarboxylic acid ester is an organotin thiomalic acid ester of claim 2.

20. The halogen-containing polymer of claim 17 wherein the organotin mercapto dicarboxylic acid ester is an organotin thiomalic acid ester of claim 3.

21. The halogen-containing polymer of claim 17 wherein the organotin mercapto dicarboxylic acid ester is an organotin thiomalic acid ester of claim 4.

22. A halogen-containing polymer of claim 18 in which the polymer is polyvinyl chloride homopolymer.

23. A halogen-containing polymer of claim 18 in which the polymer is a copolymer of a major quantity of vinyl chloride and a minor quantity of another vinyl monomer.

24. A halogen-containing polymer of claim 18, in which the amount of organotin mercapto dicarboxylic acid ester is within the range from about 0.25% to about 10% by weight of the composition.

25. A halogen-containing polymer of claim 18, including in addition a polyvalent metal salt of a carboxylic acid or alkyl phenol.

26. A halogen-containing polymer of claim 18, including in addition an epoxy compound.

27. A halogen-containing polymer of claim 18, including in addition a plasticizer for the resin in an amount in excess of about 10% by weight.

28. A rigid halogen-containing polymer of claim 18 comprising a plasticizer in an amount up to about 10% by weight of the composition.

29. A halogen-containing polymer of claim 18 including in addition a phenolic antioxidant.

30. A halogen-containing polymer of claim 18 including in addition an impact modifier.

31. A mixture of organotin mercapto dicarboxylic acid esters useful as a stabilizer for improving the resistance to deterioration of polyvinyl chloride resins when heated at 350° F, and having at least one tin atom to which organic groups are linked only through carbon and sulfur, having linked to tin through sulfur at least one mercapto dicarboxylic acid ester group, each of the organotin mercapto dicarboxylic acid esters having per tin atom one or two alkyl, cycloalkyl or alkylcycloalkyl groups attached to tin through carbon; the alkyl having from 1 to about 12 carbon atoms, the cycloalkyl having from 3 to about 12 carbon atoms, and the alkyl cycloalkyl having from 4 to about 12 carbon atoms; and two or three mercapto dicarboxylic acid ester groups attached to tin through sulfur, the mercapto dicarboxylic acid having from about 4 to about 24 carbon atoms, and having at least one esterifying group selected from the group consisting of alkyl, cycloalkyl, and alkylcycloalkyl, the alkyl having from 1 to about 12 carbon atoms, the cycloalkyl having from 3 to about 12 carbon atoms, and the alkyl cycloalkyl having from 4 to about 12 carbon atoms, and at least one esterifying group selected from the group consisting of bivalent alkylene, cycloalkylene and alkylenecycloalkylene, the alkylene having from about 2 to about 12 carbon atoms, the cycloalkylene having from 3 to about 12 carbon atoms, and the alkylenecycloalkylene having from 4 to about 12 carbon atoms, each of the two valences of the bivalent alkylene, cycloalkylene and alkylcycloalkylene being linked to groups selected from the group consisting of one hydroxyl and one carboxylic group of mercapto dicarboxylic acid; and two carboxylic acid groups of mercapto dicarboxylic acid, one of said organotin mercapto dicarboxylic acid esters having per tin atom one alkyl group linked to tin and three mercapto dicarboxylic acid ester groups esterified with alkyl and alkylene groups; and one of said organotin mercapto dicarboxylic acid esters having per tin atom two alkyl groups linked to tin, and two mercapto dicarboxylic acid ester groups esterified with alkyl and alkylene groups.

32. A mixture of organotin mercapto dicarboxylic acid esters in accordance with claim 31, having alkyl groups attached to tin through carbon, and alkyl and alkylene esterifying groups.

33. A mixture of organotin mercapto dicarboxylic acid esters in accordance with claim 32 wherein the alkyl groups attached to tin through carbon are butyl.

34. A mixture of organotin mercapto dicarboxylic acid esters in accordance with claim 32, wherein the alkyl groups attached to tin through carbon are octyl.

35. A mixture of organotin mercapto dicarboxylic acid esters in accordance with claim 32, wherein the alkyl groups attached to tin through carbon are methyl.

36. A mixture of organotin mercapto dicarboxylic acid esters in accordance with claim 32, wherein the alkyl groups attached to tin through carbon are methyl, and the alkyl esterifying groups are butyl.

37. A mixture of organotin mercapto dicarboxylic acid esters in accordance with claim 32, wherein the alkyl groups attached to tin through carbon are octyl, and the alkyl esterifying groups are butyl.

38. A polyvinyl chloride resin composition having an enhanced resistance to deterioration when heated at 350° F, comprising a polyvinyl chloride resin and a mixture of organotin mercapto dicarboxylic esters in accordance with claim 31.

39. An organotin mercapto dicarboxylic acid mixed monohydric and polyhydric alcohol ester having per tin atom one or two alkyl, cycloalkyl, or alkylcycloalkyl groups attached to tin through carbon, and two or three thiodicarboxylic acid ester groups attached to tin through sulfur, and having the formula:

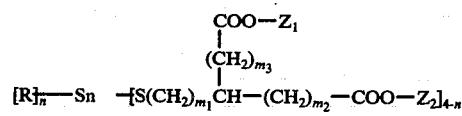

wherein $m_1$ and $m_3$ are numbers within the range from 0 to about 7;

$m_2$ is a number within the range from 1 to about 7;

$n$ is 1 or 2;

R is selected from the group consisting of alkyl, cycloalkyl, and alkycycloalkyl, the alkyl having from one to about twelve carbon atoms, the cycloalkyl having from 3 to about 12 carbon atoms, and the alkylcycloalkyl having from 4 to about 12 carbon atoms linked to tin through carbon; and at least one of $Z_1$ and $Z_2$ is selected from the group consisting of alkyl, cycloalkyl, and alkylcycloalkyl, the alkyl having from 1 to about 12 carbon atoms, the cycloalkyl having from 3 to about 12 carbon atoms, and the alkylcycloalkyl having from 4 to about 12 carbon atoms;

and at least one of $Z_1$ and $Z_2$ is selected from the group consisting of i. bivalent alkylene, cycloalkylene and alkylenecycloalkylene taken together with the other of $Z_1$ and $Z_2$ of the organotin mercapto dicarboxylic acid ester; the alkylene having from about 2 to about 12 carbon atoms, the cycloalkylene having from 3 to about 12 carbon atoms, and the alkylenecycloalkylene having from 4 to about 12 carbon atoms;

ii. hydroxyalkyl, hydroxycycloalkyl and hydroxyalkylcycloalkyl having from 2 to about 12 carbon atoms; the alkyl having from 1 to about 12 carbon atoms, the cycloalkyl having from 3 to about 12 carbon atoms, and the alkylcycloalkyl having from 4 to about 12 carbon atoms linked to tin through carbon; and iii. bivalent alkylene, cycloalkylene and alkylenecycloalkylene having from about 2 to about 12 carbon atoms and linked to a carboxylic acid ester group of a second organotin mercapto dicarboxylic acid ester; the alkylene having from about 2 to about 12 carbon atoms, the cycloalkylene having from 3 to about 12 carbon atoms, and the alkylenecycloalkylene having from 4 to about 12 carbon atoms.

40. An organotin mercapto dicarboxylic acid ester of claim 39 in which $n$ is 1.

41. An organotin mercapto dicarboxylic acid ester of claim 39, in which $n$ is 2.

42. An organotin thiomalic acid ester of claim 39, in which $m_1$ and $m_3$ are 0, and $n$ is 1.

43. An organotin thiomalic acid ester of claim 39, in which $m_1$ and $m_3$ are 0, and $n$ is 2.

44. An organotin thiomalic acid ester of claim 39, in which at least one of $Z_1$ and $Z_2$ is alkylene.

45. An organotin thiomalic acid ester of claim 39, in which at least one of $Z_1$ and $Z_2$ is methyl and at least one of $Z_1$ and $Z_2$ is ethylene.

46. An organotin thiomalic acid ester of claim 39, in which at least one of $Z_1$ and $Z_2$ is butyl and at least one of $Z_1$ and $Z_2$ is ethylene.

47. An organotin thiomalic acid ester of claim 39, in which at least one of $Z_1$ and $Z_2$ is octyl and at least one of $Z_1$ and $Z_2$ is ethylene.

* * * * *

UNITED STATES PATENT OFFICE
CERTIFICATE OF CORRECTION

Patent No. 4,058,543   Dated November 15, 1977

Inventor(s) Gerry P. Mack

It is certified that error appears in the above-identified patent and that said Letters Patent are hereby corrected as shown below:

| | | |
|---|---|---|
| Column 1, line 48 | : | "ordor" should be -- odor -- |
| line 50 | : | "order" should be -- odor -- |
| line 54 | : | "ordor" should be -- odor -- |
| Column 2, line 67 | : | "$R_n Sn(SR'(COOR'')_m)_{4-n}$ ⎮" should be -- $R_n Sn(SR'(COOR'')_m)_{4-n}$ -- |
| Column 3, line 28 | : | "ordor" should be -- odor -- |
| Column 4, line 24 | : | Delete "No.", first occurrence |
| line 27 | : | "acid" should be -- said -- |
| Column 5, line 11 | : | "numers" should be -- numbers -- |
| Column 6, line 20 Second formula | : | Add -- Ib) -- to the right of the formula |
| line 36 Third formula | : | Add -- IIa) -- to the right of the formula |
| Column 7, line 1 First formula | : | Add -- IIb) -- to the right of the formula |
| Column 8, line 2 | : | Delete "IIb)" |

UNITED STATES PATENT OFFICE
CERTIFICATE OF CORRECTION

Patent No. 4,058,543  Dated November 15, 1977

Inventor(s) Gerry P. Mack

It is certified that error appears in the above-identified patent and that said Letters Patent are hereby corrected as shown below:

Column 8, line 15 : " $n = 1:$

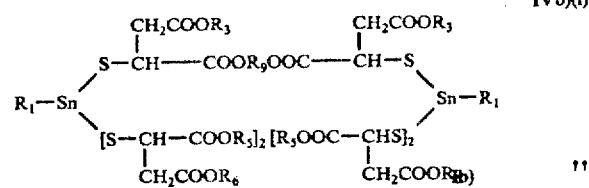

IVb)(i) "

should be $n = 1:$

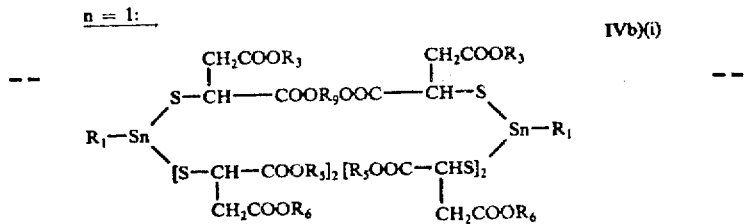

IVb)(i)

Column 8, line 39 : Delete "IIa)"

Column 9, Formula VIa)(i), third line : "SN-$R_1$" should be --Sn-$R_1$--

Column 9, Formula VIb)(1), third line : "SN-$R_1$" should be --Sn-$R_1$--

UNITED STATES PATENT OFFICE
CERTIFICATE OF CORRECTION

Patent No. 4,058,543  Dated November 15, 1977

Inventor(s) Gerry P. Mack

It is certified that error appears in the above-identified patent and that said Letters Patent are hereby corrected as shown below:

Column 9 Formula VIb)(ii):

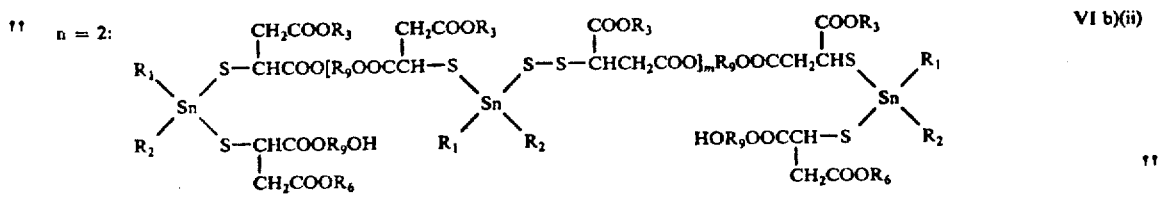

should be

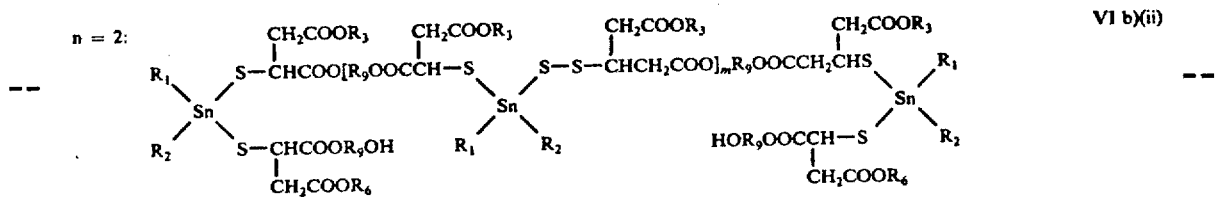

| | | |
|---|---|---|
| Column 9, line 64 | : | Insert --R_3-- after "R_2" |
| Column 10, line 13 | : | Delete "cycloalkyl", second occurrence |
| Column 11, line 20 | : | Insert at beginning of formula identification -- VIIa)-- |
| line 32 | : | Insert at beginning of formula identification -- b) -- |
| Column 11, line 50 | : | "II" second occurrence should be --III-- |
| Column 12, line 21 | : | Delete "VIIa)" |
| line 31 | : | Delete "b)" |

UNITED STATES PATENT OFFICE
CERTIFICATE OF CORRECTION

Patent No. 4,058,543　　　　Dated November 15, 1977

Inventor(s) Gerry P. Mack

It is certified that error appears in the above-identified patent and that said Letters Patent are hereby corrected as shown below:

Column 17, line 52　　　　:　"
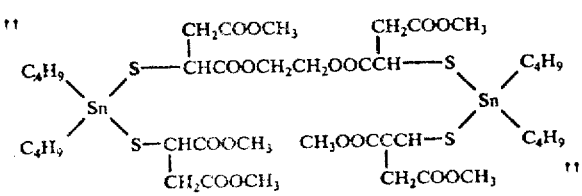
"

should be

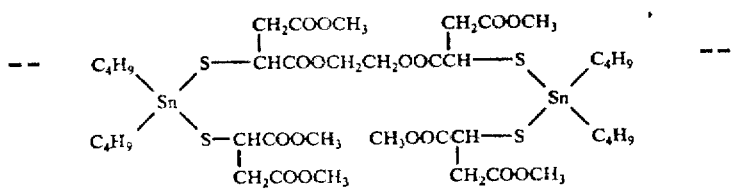

Column 18, line 2　　　　:　"
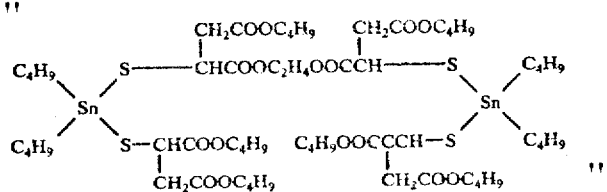
"

should be

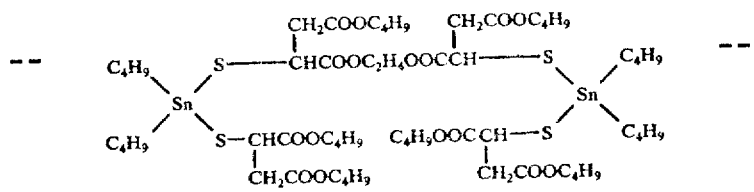

UNITED STATES PATENT OFFICE
CERTIFICATE OF CORRECTION

Patent No. 4,058,543      Dated November 15, 1977

Inventor(s) Gerry P. Mack

It is certified that error appears in the above-identified patent and that said Letters Patent are hereby corrected as shown below:

Column 18, line 20 : "

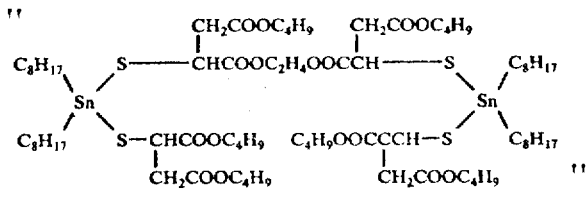

"

should be

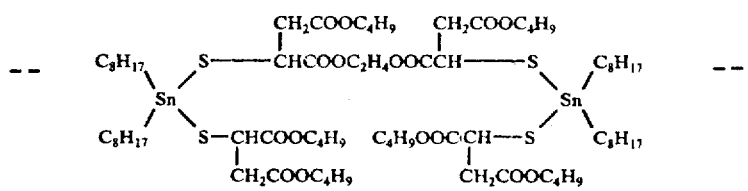

Column 18, line 35 : "

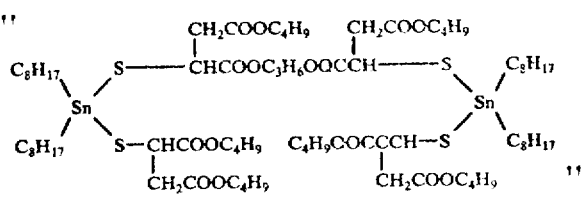

"

should be

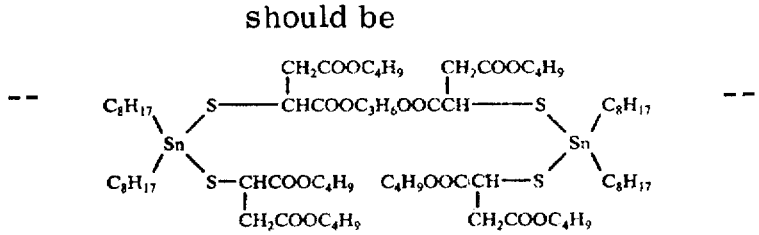

UNITED STATES PATENT OFFICE
CERTIFICATE OF CORRECTION

Patent No. 4,058,543      Dated November 15, 1977

Inventor(s) Gerry P. Mack

It is certified that error appears in the above-identified patent and that said Letters Patent are hereby corrected as shown below:

Column 19, line 17 :

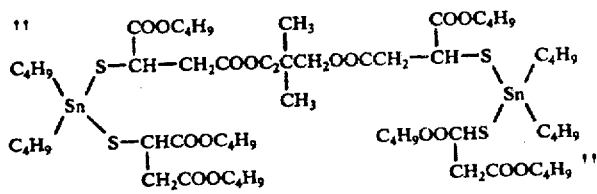

should be

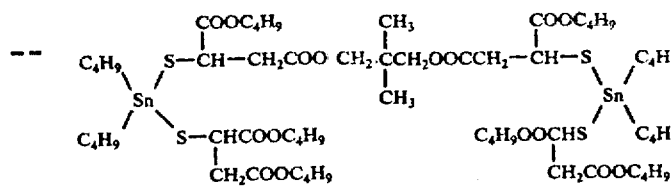

Column 19, line 55 :

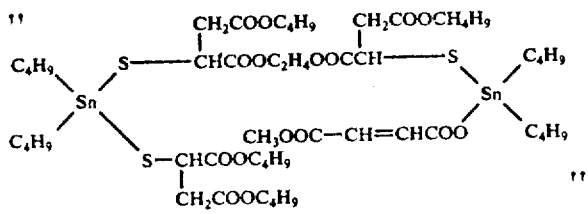

should be

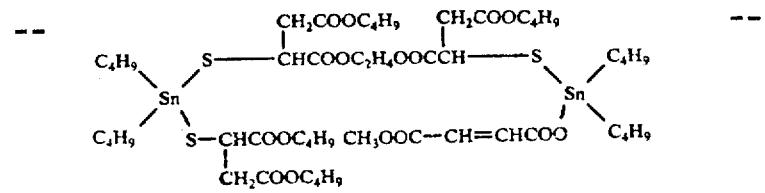

UNITED STATES PATENT OFFICE
CERTIFICATE OF CORRECTION

Patent No. 4,058,543  Dated November 15, 1977

Inventor(s) Gerry P. Mack

It is certified that error appears in the above-identified patent and that said Letters Patent are hereby corrected as shown below:

Column 21, Table VI : "

TABLE VI

|  | A | B | C | D |
|---|---|---|---|---|
| Butylethylene thiomalate | 80 g | 72 g | 72 g | 72 g |
| Butyltin trichloride | 28.2 g | 28.2 g | 28.2 g | 28.2 g |
| Sodium hydroxide | 12.0 g | 12.0 g | 11.4 g | 10.8 g |
| Weight monobutyltin butylethylene thiomalate | 91 g | 80 g | 81 g | 81 g |
| % Sn (atomic absorption) | 12.0 g. | 12.9 g | 12.8 g | 12.8 g |
| % S (iodometric) | 9.6 g | 9.5 | 9.5 | 9.4 |
| % Cl | 0.2 | 0.3 | 0.6 1.1 |  | should be

TABLE VI

|  | A | B | C | D |
|---|---|---|---|---|
| Butylethylene thiomalate | 80 g | 72 g | 72 g | 72 g |
| Butyltin trichloride | 28.2 g | 28.2 g | 28.2 g | 28.2 g |
| Sodium hydroxide | 12.0 g | 12.0 g | 11.4 g | 10.8 g |
| Weight monobutyltin butylethylene thiomalate | 91 g | 80 g | 81 g | 81 g |
| % Sn (atomic absorption) | 12.0 g | 12.9 g | 12.8 g | 12.8 g |
| % S (iodometric) | 9.6 g | 9.5 | 9.5 | 9.4 |
| % Cl | 0.2 | 0.3 | 0.6 | 1.1 |

UNITED STATES PATENT OFFICE
CERTIFICATE OF CORRECTION

Patent No. 4,058,543                     Dated November 15, 1977

Inventor(s) Gerry P. Mack

It is certified that error appears in the above-identified patent and that said Letters Patent are hereby corrected as shown below:

| | | |
|---|---|---|
| Column 25, line 53 | : | "to" should be -- of -- |
| Column 27, line 68 | : | "(dibutyltiomalate)" should be -- (dibutylthiomalate)-- |
| Column 34, line 38 | : | "tim" should be -- tin -- |
| Column 35, line 42 | : | Insert --acid-- after "carboxylic" |

Signed and Sealed this

Eighth Day of August 1978

[SEAL]

Attest:

RUTH C. MASON
Attesting Officer

DONALD W. BANNER
Commissioner of Patents and Trademarks